(12) United States Patent
Kubiak et al.

(10) Patent No.: US 8,657,820 B2
(45) Date of Patent: Feb. 25, 2014

(54) BONE PLATE AND KEEL SYSTEMS

(75) Inventors: Erik N. Kubiak, Salt Lake City, UT (US); Charles L. Saltzman, Salt Lake City, UT (US)

(73) Assignee: Tornier, Inc., Edina, MN (US)

( * ) Notice: Subject to any disclaimer, the term of this patent is extended or adjusted under 35 U.S.C. 154(b) by 143 days.

(21) Appl. No.: 13/178,460

(22) Filed: Jul. 7, 2011

(65) Prior Publication Data

US 2011/0306976 A1  Dec. 15, 2011

Related U.S. Application Data

(63) Continuation-in-part of application No. 12/577,683, filed on Oct. 12, 2009, and a continuation-in-part of application No. 12/577,688, filed on Oct. 12, 2009.

(51) Int. Cl.
*A61B 17/80* (2006.01)

(52) U.S. Cl.
USPC .......................................................... 606/70

(58) Field of Classification Search
USPC ................................ 606/70, 71, 286; 403/381
See application file for complete search history.

(56) References Cited

U.S. PATENT DOCUMENTS

| | | | |
|---|---|---|---|
| 3,039,340 A * | 6/1962 | Zimmerman | 81/177.85 |
| 5,271,737 A | 12/1993 | Baldwin et al. | |
| 5,709,682 A | 1/1998 | Medoff | |
| 5,749,875 A | 5/1998 | Puddu | |
| 6,008,433 A | 12/1999 | Stone | |
| 6,045,552 A | 4/2000 | Zucherman et al. | |
| 6,179,839 B1 | 1/2001 | Weiss et al. | |
| 7,108,697 B2 | 9/2006 | Mingozzi et al. | |
| 7,182,786 B2 | 2/2007 | Justin et al. | |
| 7,357,817 B2 | 4/2008 | D'Alessio, II | |
| 2004/0167631 A1 | 8/2004 | Luchesi et al. | |
| 2004/0204712 A1 | 10/2004 | Kolb et al. | |
| 2005/0060039 A1 | 3/2005 | Cyprien | |
| 2005/0075641 A1 | 4/2005 | Singhatat et al. | |
| 2005/0177245 A1* | 8/2005 | Leatherbury et al. | 623/23.5 |
| 2006/0142869 A1 | 6/2006 | Gross | |
| 2006/0217722 A1 | 9/2006 | Dutoit et al. | |
| 2006/0241609 A1 | 10/2006 | Myerson et al. | |
| 2006/0247650 A1 | 11/2006 | Yerby et al. | |
| 2007/0123863 A1 | 5/2007 | Winslow et al. | |
| 2007/0142917 A1 | 6/2007 | Roche et al. | |
| 2007/0282448 A1 | 12/2007 | Abdou | |
| 2010/0152782 A1* | 6/2010 | Stone et al. | 606/280 |

FOREIGN PATENT DOCUMENTS

WO  WO 99/38448  8/1999

* cited by examiner

*Primary Examiner* — Nicholas Woodall
(74) *Attorney, Agent, or Firm* — Hudak, Shunk & FFarine Co. LPA

(57) ABSTRACT

Systems and methods for stabilizing portions of bone are provided. In some aspects, a bone plate system includes a plate configured to be fastened to at least one bone portion. The plate includes a keel slot and a locking assembly. The bone plate system also includes a keel configured to extend into the at least one bone portion through the keel slot. The locking assembly is configured to substantially prevent the keel from dislodging from the plate when the keel extends into the at least one bone portion through the keel slot.

11 Claims, 42 Drawing Sheets

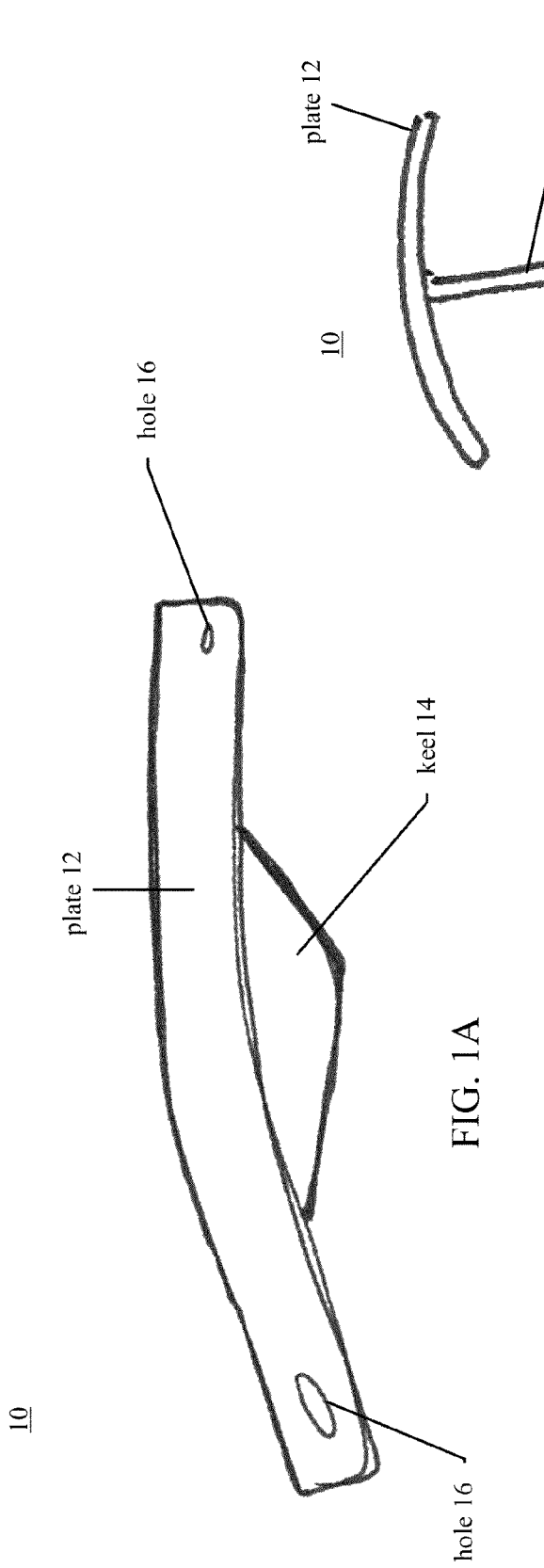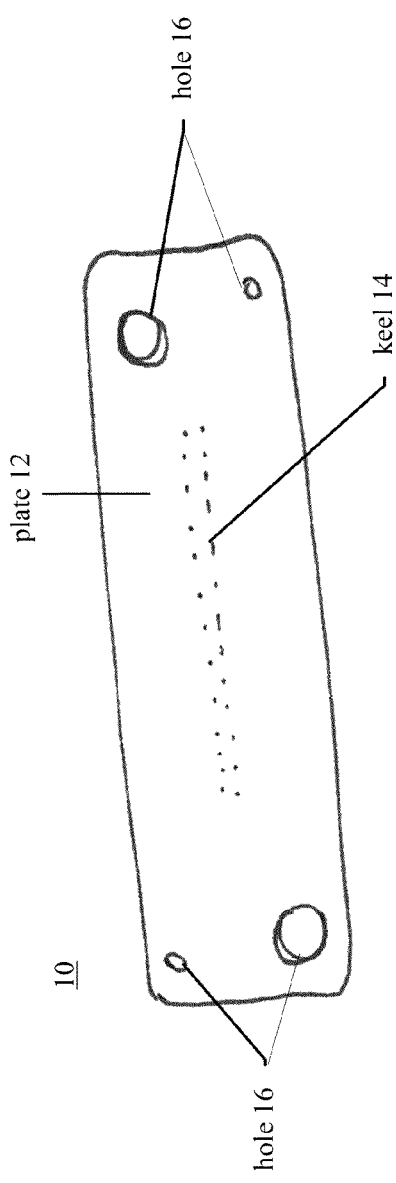
FIG. 1A
FIG. 1B
FIG. 1C

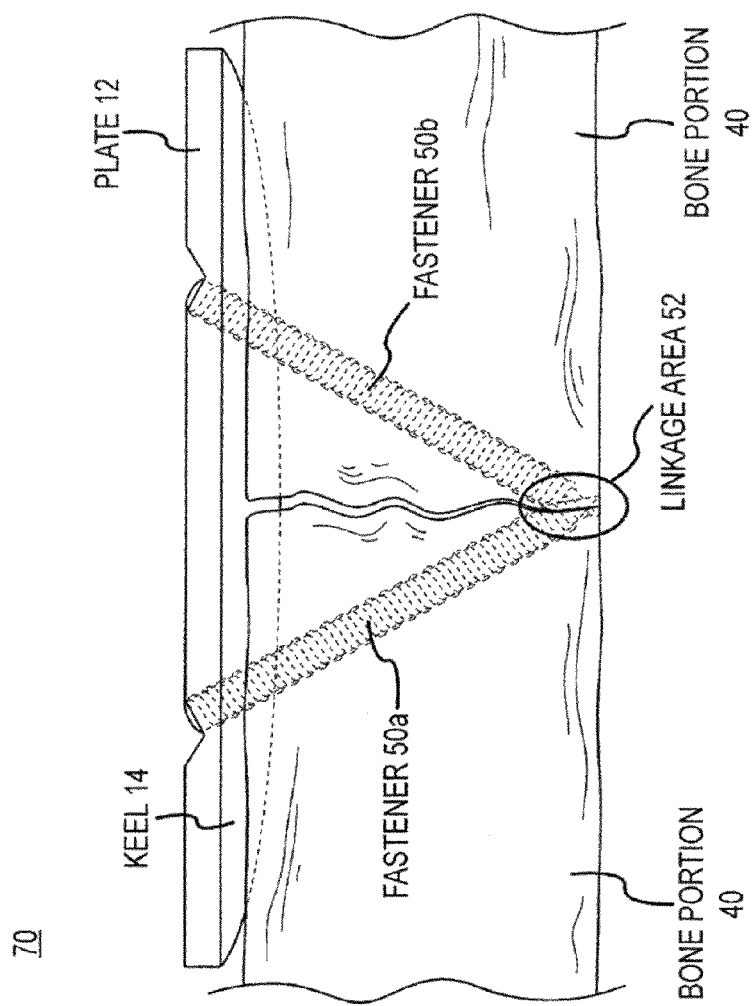

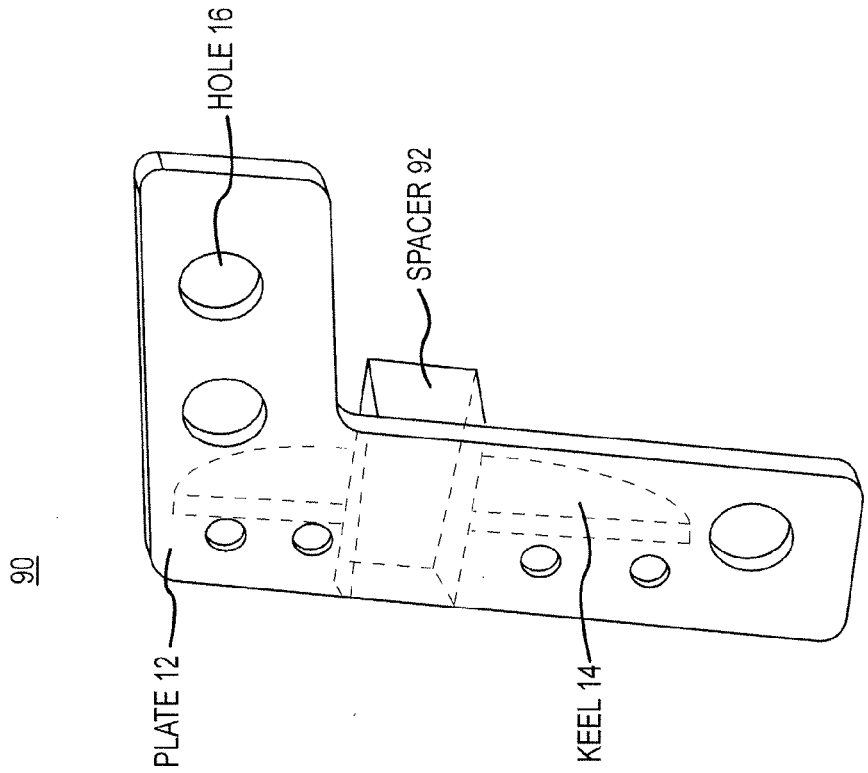
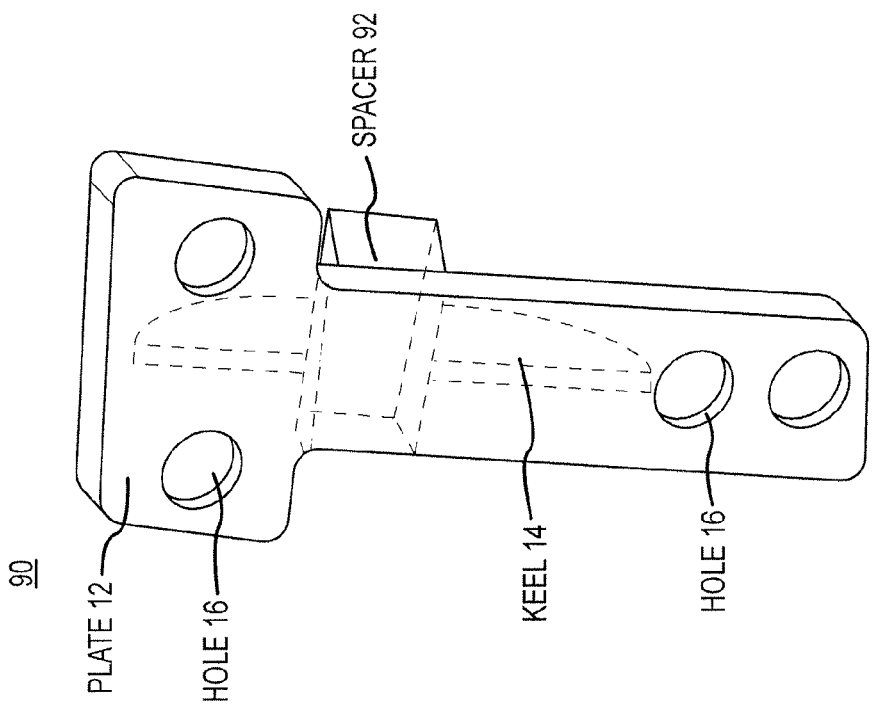
FIG. 13B
FIG. 13A

1700 contacting two bone portions with a plate, the bone portions having a joint line therebetween, the plate comprising a first hole at a first portion of the plate
1702 inserting a first fastener through the first hole into the bone portions such that the first fastener spans the joint line
1704

1800

```
┌─────────────────────────────────────────────────────────────────────┐
│ affixing a plate to a first bone portion, the plate comprising a first hole at a │
│                       first portion of the plate                    │
│                                1802                                 │
└─────────────────────────────────────────────────────────────────────┘
                                    ↓
┌─────────────────────────────────────────────────────────────────────┐
│ inserting a first fastener through the first hole into the first bone portion, and │
│  thereafter through a contact surface of the first bone portion, and thereafter │
│  through a contact surface of a second bone portion and into the second bone │
│  portion, such that when the first fastener is advanced, the contact surface of │
│   the first bone portion makes contact with the contact surface of the second │
│                              bone portion                           │
│                                1804                                 │
└─────────────────────────────────────────────────────────────────────┘
                                    ↓
┌─────────────────────────────────────────────────────────────────────┐
│ progressively advancing the first fastener such that the first and second bone │
│ portions become aligned with each other and progressively compress against │
│                              each other                             │
│                                1806                                 │
└─────────────────────────────────────────────────────────────────────┘
```

```
cutting bone to form a first groove in a first bone portion and a second bone
           portion having a joint line therebetween
                            2002
```

```
   fastening a plate to the first and second bone portions such that a first
 portion of a keel from the plate fits substantially within the first groove of
   the first bone portion, a second portion of the keel from the plate fits
  substantially within the first groove of the second bone portion, the keel
  spans the joint line, and a spacer in or on at least one of the plate and the
            keel resides between the first and second bone portions
                                   2004
```

FIG. 20

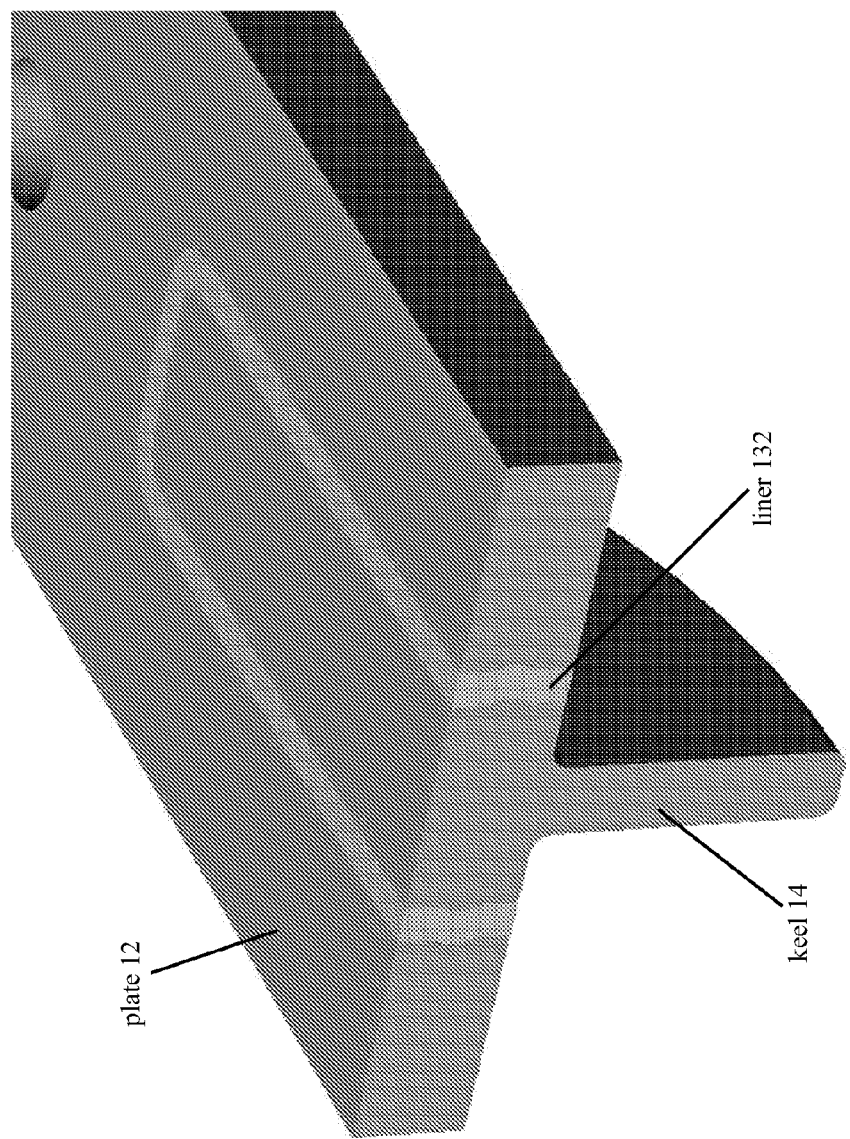

2800

```
fastening a plate to at least one bone portion, the plate having a keel slot and
a locking assembly
2802
```

```
extending a keel into the at least one bone portion through the keel slot
2804
```

```
substantially preventing, with the locking assembly, the keel from
dislodging from the plate when the keel extends into the at least one bone
portion through the keel slot
2806
```

FIG. 28

2900 fastening a plate to at least one bone portion,
wherein a keel extends from the plate in a direction away from the at least
one bone portion when the plate is fastened to the at least one bone portion
2902

FIG. 29

BONE PLATE AND KEEL SYSTEMS

RELATED APPLICATIONS

This application is a continuation-in-part of U.S. patent application Ser. No. 12/577,688, entitled "Bone Fixation Systems," filed on Oct. 12, 2009, and U.S. patent application Ser. No. 12/577,683, entitled "Bone Fixation and Compression Systems," filed on Oct. 12, 2009, both of which are hereby incorporated by reference in their entirety for all purposes.

FIELD

Some embodiments of the present inventions generally relate to bone stabilization and, in particular, relate to systems and methods for stabilizing portions of bone.

BACKGROUND

Bone plates are surgical tools used to assist in the healing of bones that are fractured or have undergone surgery. Fractures may be set and held in place using bone plates. Bone plates can be applied to fractures occurring in many bones throughout the skeleton, such as in the spine.

SUMMARY

According to various aspects of the subject disclosure, a bone plate system for stabilizing portions of bone is provided. The system may comprise a plate, having a bone engaging surface and configured to be fastened to two bone portions having a joint line therebetween. The system may also comprise a keel projecting from the bone engaging surface. The keel may extend into the bone portions and span the joint line when the plate is fastened to the bone portions. A ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08.

In certain aspects, the plate comprises a first hole in a first portion of the plate. The first hole and the plate may be configured such that when a first fastener extends through the first hole and fastens the plate to the bone portions, the first fastener spans the joint line. The plate may comprise a second hole in a second portion of the plate. The second hole may be configured to receive a second fastener therethrough for fastening the plate to the bone portions. In some aspects, the second hole and the plate may be configured such that when the second fastener extends through the second hole and fastens the plate to the bone portions, the second fastener spans the joint line. In some aspects, the system may further comprise the first and second fasteners, wherein when the first fastener and the second fastener extend through the respective holes and the plate is fastened to the bone portions, a portion of the first fastener is coupled to a portion of the second fastener. The portion of the first fastener may be coupled to the portion of the second fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the bone portions define a joint therebetween. The joint may comprise at least one of a natural joint and an artificial joint. The bone portions may be of a same bone or may be of different bones. In some aspects, the plate and the keel may be integrally formed. The plate may be substantially orthogonally coupled to the keel (e.g., within a range of 80-100 degrees). At least one of the plate and the keel may comprise at least one of steel and titanium. In some aspects, the keel may comprise porous metal.

According to certain aspects, the system may further comprise a first protrusion projecting from a first half of the bone engaging surface and configured such that when the plate is fastened to the bone portions, the first protrusion extends into at least one of the bone portions. The system may further comprise a second protrusion projecting from a second half of the bone engaging surface and configured such that when the plate is fastened to the bone portions, the second protrusion extends into at least another of the bone portions. The system may further comprise a jig having a first slot permitting cutting of bone through the first slot, the first slot spanning the joint line when the jig is fastened to the bone portions.

According to various aspects of the subject disclosure, a method for stabilizing portions of bone is provided. The method may comprise cutting bone to form a first groove in two bone portions having a joint line therebetween. The method may also comprise fastening a plate to the bone portions such that a keel from the plate fits substantially within the first groove and spans the joint line. A ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate may comprise a first hole at a first portion of the plate. The fastening the plate may comprise inserting a first fastener through the first hole into the bone portions such that the first fastener spans the joint line. In some aspects, the method may further comprise drilling bone through a first location corresponding to the first hole to form a first channel. The first fastener may fit substantially within the first channel. In some aspects, the plate may further comprise a second hole at a second portion of the plate. The fastening the plate may further comprise inserting a second fastener through the second hole into at least one of the bone portions. In some aspects, the method may further comprise drilling bone through a second location corresponding to the second hole to form a second channel. The second fastener may fit substantially within the second channel. In some aspects, the second fastener may span the joint line.

According to certain aspects, the inserting the second fastener may comprise inserting the second fastener such that a portion of the second fastener is coupled to a portion of the first fastener. The portion of the second fastener may be coupled to the portion of the first fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the bone portions define a joint therebetween. The joint may comprise at least one of a natural joint and an artificial joint. The bone portions may be of a same bone or may be of different bones. In some aspects, the plate and the keel may be integrally formed. The plate may be substantially orthogonally coupled to the keel. At least one of the plate and the keel may comprise at least one of steel and titanium. In some aspects, the keel may comprise porous metal.

In some aspects, the method may further comprise fastening a jig to the bone portions. The jig may comprise a first slot permitting cutting of bone through the first slot. The first slot may span the joint line when the jig is fastened to the bone portions. The cutting may comprise cutting bone through the first slot to form the first groove. In some aspects, the jig may comprise a second slot permitting cutting of bone through the second slot. The method may further comprise cutting bone through the second slot to form a second groove in at least one of the bone portions. The fastening the plate may comprise fastening the plate to the bone portions such that a protrusion from the plate fits substantially within the second groove.

According to various aspects of the subject disclosure, a bone plate system for stabilizing portions of bone is provided. The system may comprise a plate comprising a first hole in a first portion of the plate. The system may also comprise a first fastener configured to extend through the first hole and fasten the plate to two bone portions having a joint line therebetween. When the first fastener extends through the first hole and fastens the plate to the bone portions, the first fastener may span the joint line.

In some aspects, the plate may further comprise a second hole in a second portion of the plate. The system may further comprise a second fastener. The second fastener may be configured to extend through the second hole and fasten the plate to the bone portions. When the second fastener extends through the second hole and fastens the plate to the bone portions, the second fastener may span the joint line.

According to certain aspects, when the first fastener and the second fastener extend through the respective holes and the plate is fastened to the bone portions, a portion of the first fastener may be coupled to a portion of the second fastener. The portion of the first fastener may be coupled to the portion of the second fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density. In some aspects, the bone portions define a joint therebetween. The joint may comprise at least one of a natural joint and an artificial joint. The bone portions may be of a same bone or may be of different bones.

In some aspects, the system may further comprise a keel. The plate may comprise a bone engaging surface and the keel may project from the bone engaging surface. The keel may extend into the bone portions and span the joint line when the plate is fastened to the bone portions. A ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08. In some aspects, the plate and the keel may be integrally formed. The plate may be substantially orthogonally coupled to the keel. At least one of the plate and the keel may comprise at least one of steel and titanium. In some aspects, the keel may comprise porous metal.

In some aspects, the system may further comprise a jig having a first slot permitting cutting of bone through the first slot. The first slot may span the joint line when the jig is fastened to the bone portions. In some aspects, the plate may comprise a bone engaging surface and the system may further comprise a first protrusion projecting from a first half of the bone engaging surface. The first protrusion may be configured such that when the plate is fastened to the bone portions, the first protrusion extends into at least one of the bone portions. The plate may further comprise a second protrusion projecting from a second half of the bone engaging surface and be configured such that when the plate is fastened to the bone portions, the second protrusion extends into at least another of the bone portions.

According to various aspects of the subject disclosure, a method for stabilizing portions of bone is provided. The method may comprise contacting two bone portions with a plate. The bone portions may have a joint line therebetween. The plate may comprise a first hole at a first portion of the plate. The method may also comprise inserting a first fastener through the first hole into the bone portions such that the first fastener spans the joint line.

In some aspects, the method may further comprise drilling bone through a first location corresponding to the first hole to form a first channel. The first fastener may fit substantially within the first channel. The plate may further comprise a second hole at a second portion of the plate. The method may further comprise inserting a second fastener through the second hole into at least one of the bone portions. In some aspects, the method may further comprise drilling bone through a second location corresponding to the second hole to form a second channel. The second fastener may fit substantially within the second channel. In some aspects, the second fastener may span the joint line.

According to certain aspects, the inserting the second fastener may comprise inserting the second fastener such that a portion of the second fastener is coupled to a portion of the first fastener. The portion of the second fastener may be coupled to the portion of the first fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the bone portions define a joint therebetween. The joint may comprise at least one of a natural joint and an artificial joint. The bone portions may be of a same bone or may be of different bones.

In some aspects, the method may further comprise cutting bone to form a first groove in the bone portions. The method may further comprise fastening the plate to the bone portions such that a keel from the plate fits substantially within the first groove and spans the joint line. A ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate and the keel may be integrally formed. The plate may be substantially orthogonally coupled to the keel. At least one of the plate and the keel may comprise at least one of steel and titanium. In some aspects, the keel may comprise porous metal.

In some aspects, the method may further comprise fastening a jig to the bone portions. The jig may comprise a first slot permitting cutting of bone through the first slot. The first slot may span the joint line when the jig is fastened to the bone portions. The cutting may comprise cutting bone through the first slot to form the first groove. In some aspects, the jig may comprise a second slot permitting cutting of bone through the second slot. The method may further comprise cutting bone through the second slot to form a second groove in at least one of the bone portions. The fastening the plate may comprise fastening the plate to the bone portions such that a protrusion from the plate fits substantially within the second groove.

According to various aspects of the subject disclosure, a method for stabilizing and compressing portions of bone is provided. The method may comprise affixing a plate to a first bone portion. The plate may comprise a first hole at a first portion of the plate. The method may also comprise inserting a first fastener through the first hole into the first bone portion, and thereafter through a contact surface of the first bone portion, and thereafter through a contact surface of a second bone portion and into the second bone portion, such that when the first fastener is advanced, the contact surface of the first bone portion makes contact with the contact surface of the second bone portion. The method may also comprise progressively advancing the first fastener such that the first and second bone portions become aligned with each other and progressively compress against each other.

In some aspects, the plate may further comprise a second hole at a second portion of the plate. The method may further comprise inserting a second fastener through the second hole into the second bone portion. The inserting the second fastener may comprise inserting the second fastener through the contact surface of the second bone portion, and thereafter through the contact surface of the first bone portion and into the first bone portion. In some aspects, the inserting the second fastener may comprise inserting the second fastener through the second hole into the second bone portion such that a portion of the second fastener is coupled to a portion of the first fastener. The portion of the second fastener may be coupled to the portion of the first fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the first bone portion and the second bone portion may define a joint therebetween. The joint may comprise at least one of a natural joint and an artificial joint. The first bone portion and the second bone portion may be of a same bone or may be of different bones.

According to certain aspects, the method may further comprise cutting bone to form a first groove in the first and second bone portions. The first and second bone portions may have a joint line therebetween. The method may further comprise fastening the plate to the first and second bone portions such that a keel from the plate fits substantially within the first groove and spans the joint line. A ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08. In some aspects, the plate and the keel may be integrally formed. The plate may be substantially orthogonally coupled to the keel. At least one of the plate and the keel may comprise at least one of steel and titanium. In some aspects, the keel may comprise porous metal.

In some aspects, the method may further comprise fastening a jig to the first and second bone portions. The jig may comprise a first slot permitting cutting of bone through the first slot. The first slot may span the joint line when the jig is fastened to the bone portions. The cutting may comprise cutting bone through the first slot to form the first groove. The jig may comprise a second slot permitting cutting of bone through the second slot. The method may further comprise cutting bone through the second slot to form a second groove in at least one of the first bone portion and the second bone portion. The fastening the plate may comprise fastening the plate to the first and second bone portions such that a protrusion from the plate fits substantially within the second groove.

According to various aspects of the subject disclosure, a bone plate system for stabilizing and compressing portions of bone is provided. The system may comprise a plate, having a bone engaging surface and configured to be fastened to a first bone portion and a second bone portion having a joint line therebetween. The system may also comprise a keel projecting from the bone engaging surface. The keel may extend into the first and second bone portions and span the joint line when the plate is fastened to the first and second bone portions. The system may also comprise a fin projecting from the keel. The fin may be configured such that as the plate is fastened to the first and second bone portions, the fin (a) is inserted through a contact surface of the second bone portion and into the second bone portion, and thereafter (b) is progressively advanced into the second bone portion such that a contact surface of the first bone portion makes contact with the contact surface of the second bone portion.

In some aspects, the fin may further be configured such that (a) as the plate is fastened to the first and second bone portions and (b) after the contact surface of the first bone portion makes contact with the contact surface of the second bone portion, the fin is progressively advanced into the second bone portion such that the first and second bone portions become aligned with each other and progressively compress against each other. In some aspects, a long axis of the fin and a long axis of the plate may be substantially non-parallel. The fin may further be configured such that (a) as the plate is fastened to the first and second bone portions and (b) as the fin is progressively advanced into the second bone portion, the fin moves in the second bone portion in a direction away from the contact surface of the second bone portion and away from the plate.

In some aspects, a ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate may comprise a first hole in a first portion of the plate. The first hole and the plate may be configured such that when a first fastener extends through the first hole and fastens the plate to the first and second bone portions, the first fastener spans the joint line. The plate may comprise a second hole in a second portion of the plate. The second hole may be configured to receive a second fastener therethrough for fastening the plate to the first and second bone portions. The second hole and the plate may be configured such that when the second fastener extends through the second hole and fastens the plate to the first and second bone portions, the second fastener spans the joint line.

According to certain aspects, the system may further comprise the first and second fasteners. When the first fastener and the second fastener extend through the respective holes and the plate is fastened to the first and second bone portions, a portion of the first fastener may be coupled to a portion of the second fastener. The portion of the first fastener may be coupled to the portion of the second fastener through at least one of interdigitation, locking, adhesion, and fusion. In some aspects, the system may further comprise the first and second fasteners. At least one of the first fastener and the second fastener may comprise at least one of titanium and cobalt. In some aspects, the first fastener may comprise a metal of a first density, and the second fastener may comprise a metal of a second density different from the first density.

In some aspects, the bone portions define a joint therebetween. The joint may comprise at least one of a natural joint and an artificial joint. The bone portions may be of a same bone or may be of different bones. In some aspects, at least one of (a) the plate and the keel and (b) the keel and the fin are integrally formed. In some aspects, at least one of (a) the plate and the keel and (b) the keel and the fin are substantially orthogonally coupled to each other. At least one of the plate, the keel, and the fin may comprise at least one of steel and titanium. In some aspects, at least one of the keel and the fin may comprise porous metal.

In some aspects, the system may further comprise a first protrusion projecting from a first half of the bone engaging surface and be configured such that when the plate is fastened to the first and second bone portions, the first protrusion extends into at least one of the first bone portion and the second bone portion. The system may further comprise a second protrusion projecting from a second half of the bone engaging surface and be configured such that when the plate is fastened to the first and second bone portions, the second protrusion extends into at least one of the first bone portion and the second bone portion. In some aspects, the system may further comprise a jig having a first slot permitting cutting of bone through the first slot. The first slot may span the joint line when the jig is fastened to the first and second bone portions.

According to various aspects of the subject disclosure, a method for stabilizing and compressing portions of bone is provided. The method may comprise cutting bone to form a first groove in a first bone portion and a second bone portion. The first bone portion and the second bone portion may have a joint line therebetween. The method may also comprise fastening the plate to the first bone portion such that a first portion of a keel from the plate fits substantially within the first groove of the first bone portion. The method may also comprise fastening the plate to the second bone portion such that the keel spans the joint line and a fin from the keel (a) is inserted through a contact surface of the second bone portion and into the second bone portion, and thereafter (b) is progressively advanced into the second bone portion such that (i) a contact surface of the first bone portion makes contact with the contact surface of the second bone portion and (ii) a second portion of the keel fits substantially within the first groove of the second bone portion.

In some aspects, the fastening the plate to the second bone portion may comprise progressively advancing the fin into the second bone portion, after the contact surface of the first bone portion makes contact with the contact surface of the second bone portion, such that the first and second bone portions become aligned with each other and progressively compress against each other. A long axis of the fin and a long axis of the plate may be substantially non-parallel. In some aspects, the fastening the plate to the second bone portion may comprise moving the fin in the second bone portion in a direction away from the contact surface of the second bone portion and away from the plate as the fin is progressively advanced into the second bone portion.

In some aspects, a ratio of an average thickness of the plate to an average width of the plate may be less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate may comprise a first hole at a first portion of the plate. The method may further comprise inserting a first fastener through the first hole into at least one of the first bone portion and the second bone portion such that the first fastener spans the joint line. The inserting the first fastener may comprise drilling bone through a first location corresponding to the first hole to form a first channel. The first fastener may fit substantially within the first channel. In some aspects, the plate may further comprise a second hole at a second portion of the plate. The method may further comprise inserting a second fastener through the second hole into at least one of the first bone portion and the second bone portion. The inserting the second fastener may comprise drilling bone through a second location corresponding to the second hole to form a second channel. The second fastener may fit substantially within the second channel. In some aspects, the second fastener may span the joint line.

According to certain aspects, the inserting the second fastener may comprise inserting the second fastener such that a portion of the second fastener is coupled to a portion of the first fastener. The portion of the second fastener may be coupled to the portion of the first fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the first bone portion and the second bone portion define a joint therebetween. The joint may comprise at least one of a natural joint and an artificial joint. The first bone portion and the second bone portion may be of a same bone or may be of different bones. In some aspects, at least one of (a) the plate and the keel and (b) the keel and the fin are integrally formed. In some aspects, at least one of (a) the plate and the keel and (b) the keel and the fin are substantially orthogonally coupled to each other. At least one of the plate, the keel, and the fin may comprise at least one of steel and titanium. In some aspects, at least one of the keel and the fin may comprise porous metal.

In some aspects, the method may further comprise fastening a jig to the first and second bone portions. The jig may comprise a first slot permitting cutting of bone through the first slot. The first slot may span the joint line when the jig is fastened to the first and second bone portions. The cutting may comprise cutting bone through the first slot to form the first groove. In some aspects, the jig may comprise a second slot permitting cutting of bone through the second slot. The method may further comprise cutting bone through the second slot to form a second groove in at least one of the first bone portion and the second bone portion. In some aspects, at least one of the fastening the plate to the first bone portion and the fastening the plate to the second bone portion may comprise fastening the plate to a respective bone portion such that a protrusion from the plate fits substantially within the second groove.

According to various aspects of the subject disclosure, a bone plate system for stabilizing portions of bone is provided. The system may comprise a plate, having a bone engaging surface and configured to be fastened to two bone portions having a joint line therebetween. The system may also comprise a keel projecting from the bone engaging surface. The keel may extend into the bone portions and span the joint line when the plate is fastened to the bone portions. The system may also comprise a spacer in or on at least one of the plate and the keel, and be configured to reside between the bone portions when the plate is fastened to the bone portions.

In some aspects, the spacer may be reversibly coupled to at least one of the plate and the keel. In some aspects, the spacer may friction fit into or onto at least one of the plate and the keel. At least one of the plate and the keel may comprise a fixation portion, and the spacer may comprise at least one of a notch and a thread engaging the fixation portion. In some aspects, at least one of the plate and the keel may comprise a fixation portion that engages the spacer. The fixation portion may fit substantially within a correspondingly sized opening in the spacer.

In some aspects, a ratio of an average thickness of the plate to an average width of the plate is less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate may comprise a first hole in a first portion of the plate. The first hole and the plate may be configured such that when a first fastener extends through the first hole and fastens the plate to the bone portions, the first fastener spans the joint line. The plate may comprise a second hole in a second portion of the plate. The second hole may be configured to receive a second fastener therethrough for fastening the plate to the bone portions. The second hole and the plate may be configured such that when the second fastener extends through the second hole and fastens the plate to the bone portions, the second fastener spans the joint line.

According to certain aspects, the system may further comprise the first and second fasteners. When the first fastener and the second fastener extend through the respective holes and the plate is fastened to the bone portions, a portion of the first fastener may be coupled to a portion of the second fastener. The portion of the first fastener may be coupled to the portion of the second fastener through at least one of interdigitation, locking, adhesion, and fusion. In some aspects, the system may further comprise the first and second fasteners, and at least one of the first fastener and the second fastener may comprise at least one of titanium and cobalt. In some aspects, the first fastener may comprise a metal of a first density, and the second fastener may comprise a metal of a second density different from the first density.

In some aspects, the bone portions define a joint therebetween. The joint may comprise at least one of a natural joint and an artificial joint. The bone portions may be of a same bone or may be of different bones. In some aspects, at least one of (a) the plate and the keel, (b) the keel and the spacer, and (c) the plate and the spacer are integrally formed. In some aspects, at least one of (a) the plate and the keel, (b) the keel and the spacer, and (c) the plate and the spacer are substantially orthogonally coupled to each other. At least one of the plate, the keel, and the spacer may comprise at least one of steel and titanium. In some aspects, at least one of the keel and the spacer may comprise porous metal.

In some aspects, the system may further comprise a first protrusion projecting from a first half of the bone engaging surface and configured such that when the plate is fastened to the bone portions, the first protrusion extends into at least one of the bone portions. The system may further comprise a second protrusion projecting from a second half of the bone engaging surface and configured such that when the plate is fastened to the bone portions, the second protrusion extends into at least another of the bone portions. In some aspects, the system may further comprise a jig having a first slot permitting cutting of bone through the first slot. The first slot may span the joint line when the jig is fastened to the bone portions.

According to various aspects of the subject disclosure, a method for stabilizing portions of bone is provided. The method may comprise cutting bone to form a first groove in a first bone portion and a second bone portion having a joint line therebetween. The method may also comprise fastening a plate to the first and second bone portions such that a first portion of a keel from the plate fits substantially within the first groove of the first bone portion, a second portion of the keel from the plate fits substantially within the first groove of the second bone portion, the keel spans the joint line, and a spacer in or on at least one of the plate and the keel resides between the first and second bone portions.

In some aspects, the spacer may be reversibly coupled to at least one of the plate and the keel. In some aspects, the spacer may friction fit into or onto at least one of the plate and the keel. At least one of the plate and the keel may comprise a fixation portion, and the spacer may comprise at least one of a notch and a thread engaging the fixation portion. In some aspects, at least one of the plate and the keel may comprise a fixation portion that engages the spacer. The fixation portion may fit substantially within a correspondingly sized opening in the spacer.

In some aspects, a ratio of an average thickness of the plate to an average width of the plate is less than or equal to about 0.11. In some aspects, the ratio may be less than or equal to about 0.10. In some aspects, the ratio may be less than or equal to about 0.09. In some aspects, the ratio may be less than or equal to about 0.08.

In some aspects, the plate may comprise a first hole at a first portion of the plate. The fastening the plate may comprise inserting a first fastener through the first hole into the first and second bone portions such that the first fastener spans the joint line. In some aspects, the method may further comprise drilling bone through a first location corresponding to the first hole to form a first channel. The first fastener may fit substantially within the first channel. In some aspects, the plate may further comprise a second hole at a second portion of the plate. The fastening the plate may further comprise inserting a second fastener through the second hole into at least one of the first bone portion and the second bone portion. The method may further comprise drilling bone through a second location corresponding to the second hole to form a second channel. The second fastener may fit substantially within the second channel. In some aspects, the second fastener may span the joint line.

According to certain aspects, the inserting the second fastener may comprise inserting the second fastener such that a portion of the second fastener is coupled to a portion of the first fastener. The portion of the second fastener may be coupled to the portion of the first fastener through at least one of interdigitation, locking, adhesion, and fusion. At least one of the first fastener and the second fastener may comprise at least one of titanium and cobalt. In some aspects, the first fastener may comprise a metal of a first density, and the second fastener may comprise a metal of a second density different from the first density.

In some aspects, the first and second bone portions define a joint therebetween. The joint may comprise at least one of a natural joint and an artificial joint. The first and second bone portions may be of a same bone or may be of different bones. In some aspects, at least one of (a) the plate and the keel, (b) the keel and the spacer, and (c) the plate and the spacer are integrally formed. In some aspects, at least one of (a) the plate and the keel, (b) the keel and the spacer, and (c) the plate and the spacer are substantially orthogonally coupled to each other. At least one of the plate, the keel, and the spacer may comprise at least one of steel and titanium. In some aspects, at least one of the keel and the spacer may comprise porous metal.

In some aspects, the method may further comprise fastening a jig to the first and second bone portions. The jig may comprise a first slot permitting cutting of bone through the first slot. The first slot may span the joint line when the jig is fastened to the bone portions. The cutting may comprise cutting bone through the first slot to form the first groove. In some aspects, the jig may comprise a second slot permitting cutting of bone through the second slot. The method may further comprise cutting bone through the second slot to form a second groove in at least one of the first bone portion and the second bone portion. The fastening the plate may comprise fastening the plate to the first and second bone portions such that a protrusion from the plate fits substantially within the second groove.

According to various aspects of the subject disclosure, a bone plate system for stabilizing portions of bone is provided. The system comprises a plate configured to be fastened to at least one bone portion. The plate includes a keel slot and a locking assembly. The system also comprises a keel configured to extend into the at least one bone portion through the keel slot. The locking assembly is configured to substantially prevent the keel from dislodging from the plate when the keel extends into the at least one bone portion through the keel slot.

In some aspects, the at least one bone portion comprises two bone portions having a joint line therebetween. The keel slot is configured to span the joint line when the plate is fastened to the two bone portions. In some aspects, the keel is configured to span the joint line when the keel extends into the two bone portions through the keel slot.

According to certain aspects, the locking assembly comprises a first lip region extending along a first wall of the keel slot. The locking assembly comprises a second lip region extending along a second wall of the keel slot, the second wall being opposite the first wall. The locking assembly is configured to flex between a first state and a second state. The first and second lip regions are farther apart from one another in the first state than when the first and second lip regions are in the second state.

In some aspects, the second lip region is angled toward the at least one bone portion at less than or equal to 90 degrees from the second wall when the plate is fastened to the at least one bone portion. The first lip region is angled toward the at least one bone portion at less than or equal to 90 degrees from the first wall when the plate is fastened to the at least one bone portion. In some aspects, the first wall is slanted such that the keel slot is narrower at a first edge of the first wall than at a second edge of the first wall, wherein the first edge of the first wall is closer to the at least one bone portion than the second edge of the first wall when the plate is fastened to the at least one bone portion.

In some aspects, a keel-engaging side of the first lip region is slanted such that the keel slot is narrower at a first edge of the first lip region than at a second edge of the first lip region, wherein the first edge of the first lip region is closer to the at least one bone portion than the second edge of the first lip region when the plate is fastened to the at least one bone portion. In some aspects, the first wall and the keel-engaging side of the first lip region are slanted at substantially the same angle. In some aspects, the keel comprises one or more ridges extending along a first side of the keel. The one or more ridges are sized to fit against the first wall and the first lip region.

According to certain aspects, the locking assembly comprises a first groove region extending along a first wall of the keel slot. The keel comprises a first projection region extending along a first side of the keel, wherein the first projection region is sized to fit within the first groove region when the keel extends into the at least one bone portion. In some aspects, the locking assembly comprises a second groove region extending along a second wall of the keel slot, wherein the second wall is opposite the first wall. In some aspects, the keel comprises a second projection region, wherein the second projection region extends along a second side of the keel. In some aspects, the second projection region is sized to fit within the second groove region when the keel extends into the at least one bone portion.

According to certain aspects, the locking assembly comprises a fastener hole formed on the plate. The fastener hole is configured to receive a fastener therethrough for fastening the keel to the plate when the keel extends into the at least one bone portion. The keel comprises a corresponding fastener hole. The corresponding fastener hole is configured to receive the fastener therethrough for fastening the keel to the plate when the keel extends into the at least one bone portion. In some aspects, the corresponding fastener hole of the keel is formed on a tab region of the keel. The tab region extends from a head region of the keel and is configured to engage the fastener hole of the plate when the keel extends into the at least one bone portion. In some aspects, a tip of the keel is curved or sharp. In some aspects, the keel is configured to extend into the at least one bone portion through the keel slot when the plate is fastened to the at least one bone portion.

In some aspects, the system further comprises a liner configured to substantially prevent contact between the plate and the keel. In some aspects, the liner comprises polyether ether ketone (PEEK). In some aspects, the locking assembly comprises a liner positioned in the keel slot. The liner is configured to substantially prevent contact between the plate and the keel. In some aspects, the liner is configured to conform to a surface of the plate and to a surface of the keel.

According to various aspects of the subject disclosure, a method for stabilizing portions of bone is provided. The method comprises: fastening a plate to at least one bone portion, the plate having a keel slot and a locking assembly; extending a keel into the at least one bone portion through the keel slot; and substantially preventing, with the locking assembly, the keel from dislodging from the plate when the keel extends into the at least one bone portion through the keel slot.

In some aspects, the locking assembly comprises (i) a first lip region extending along a first wall of the keel slot and (ii) a second lip region extending along a second wall of the keel slot. The second wall is opposite the first wall. The method further comprises flexing the locking assembly between a first state and a second state, wherein the first and second lip regions are farther apart from one another in the first state than when the first and second lip regions are in the second state.

In some aspects, the method further comprises receiving a fastener through (i) a fastener hole formed on the plate and (ii) a corresponding fastener hole formed on the keel, for fastening the keel to the plate when the keel extends into the at least one bone portion. In some aspects, the keel extends into the at least one bone portion through the keel slot when the plate is fastened to the at least one bone portion. In some aspects, the method further comprises permitting cutting of bone through the keel slot when the plate is fastened to the at least one bone portion. In some aspects, the method further comprises cutting bone through the keel slot when the plate is fastened to the at least one bone portion to form a groove in the at least one bone portion. In some aspects, the keel extends into the groove through the keel slot.

According to various aspects of the subject disclosure, a bone plate system for stabilizing portions of bone is provided. The system comprises a plate configured to be fastened to at least one bone portion. The plate includes a keel slot and a locking assembly. The system also comprises a keel configured to extend into the at least one bone portion through the keel slot. The locking assembly is configured to substantially prevent the keel from dislodging from the at least one bone portion when the keel extends into the at least one bone portion through the keel slot.

According to various aspects of the subject disclosure, a bone plate system for stabilizing portions of bone is provided. The system comprises a plate configured to be fastened to at least one bone portion. The plate includes a keel slot and a locking assembly. The system also comprises a keel configured to extend into the at least one bone portion through the keel slot. The locking assembly is configured to substantially lock the keel to the plate when the keel extends into the at least one bone portion through the keel slot.

According to various aspects of the subject disclosure, a bone plate system for stabilizing portions of bone. The system comprises a plate configured to be fastened to at least one bone portion. The system also comprises a keel extending from the plate in a direction away from the at least one bone portion when the plate is fastened to the at least one bone portion.

In some aspects, the keel is integral with the plate. In some aspects, the plate comprises a first surface and a second surface, wherein the first surface is a bone engaging surface and the second surface is opposite the first surface. In some aspects, the keel projects from the second surface. In some aspects, a body region of the keel tapers away from the second surface. In some aspects, a tip of the keel is curved.

According to various aspects of the subject disclosure, a method for stabilizing portions of bone is provided. The method comprises fastening a plate to at least one bone portion. A keel extends from the plate in a direction away from the at least one bone portion when the plate is fastened to the at least one bone portion.

In some aspects, the at least one bone portion comprises two bone portions having a joint line therebetween. The keel is configured to span the joint line when the plate is fastened to the two bone portions. In some aspects, the fastening comprises inserting a fastener through a hole in the plate into the at least one bone portion such that the fastener spans the joint line.

According to various aspects of the subject disclosure, a method is provided for stabilizing and compressing first and second bone portions having a joint line therebetween. The method comprises affixing a plate to the first bone portion. The plate comprises a first hole at a first portion of the plate. The method also comprises inserting a first fastener through the first opening into the first bone portion, and thereafter through a contact surface of the first bone portion, and thereafter across the joint line, through a contact surface of a second bone portion, and into the second bone portion, such that when the first fastener is advanced, the contact surface of the first bone portion makes contact with the contact surface of the second bone portion. The method also comprises progressively advancing the first fastener such that the first and second bone portions become aligned with each other and progressively compress against each other. The method also comprises cutting bone to form a groove in the first and second bone portions. The method also comprises fastening the plate to the first and second bone portions such that a keel extending from the plate fits substantially within the groove and spans the joint line.

In some aspects, the plate further comprises a second opening at a second portion of the plate, and the method further comprises inserting a second fastener through the second opening into the second bone portion. In some aspects, the inserting the second fastener comprises inserting the second fastener through the contact surface of the second bone portion, and thereafter through the contact surface of the first bone portion and into the first bone portion. In some aspects, the inserting the second fastener comprises inserting the second fastener through the second opening into the second bone portion such that a portion of the second fastener is coupled to a portion of the first fastener. In some aspects, the portion of the second fastener is coupled to the portion of the first fastener through at least one of interdigitation, locking, adhesion, and fusion. In some aspects, the keel is configured to couple to the plate. In some aspects, the keel reversibly couples to the plate.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIGS. 1A, 1B, and 1C illustrate an example of a bone plate system, in accordance with various aspects of the subject disclosure.

FIGS. 11A, 11B, 11C, and 11D illustrate various configurations of a bone plate system, in accordance with various aspects of the subject disclosure.

FIGS. 13A and 13B illustrate examples of a bone plate system, in accordance with various aspects of the subject disclosure.

FIG. 18 illustrates an example of a method for stabilizing and compressing portions of bone, in accordance with various aspects of the subject disclosure.

FIG. 20 illustrates an example of a method for stabilizing portions of bone, in accordance with various aspects of the subject disclosure.

FIGS. 27A, 27B, 27C, and 27D illustrate various views of a liner being used to prevent contact between a keel and a plate, in accordance with various aspects of the subject disclosure.

FIG. 28 illustrates an example of a method for stabilizing portions of bone, in accordance with various aspects of the subject disclosure.

FIG. 29 illustrates an example of a method for stabilizing portions of bone, in accordance with various aspects of the subject disclosure.

DETAILED DESCRIPTION

Figure 2C:
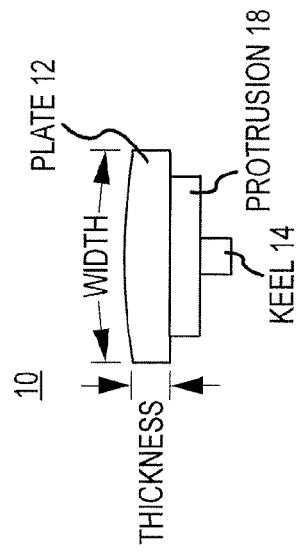
FIGS. 2A, 2B, and 2C illustrate an example of a bone plate system with one or more protrusions, in accordance with various aspects of the subject disclosure.

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Bone plates may be used in orthopedic surgery as a means to affix bones to each other to promote healing. One disadvantage of these plates, for example in relation to the use of these plates in foot surgery, is in their thickness profile. The extreme thickness of these plates may result in soft tissue irritation in the area surrounding the plate. Unfortunately, the thickness of these plates may relate directly to their strength. Therefore, thickness of these plates may not be modified without affecting the strength of the plates. Reducing the thickness of the plate, in an attempt to reduce soft tissue irritation may lead to plate failure.

According to various aspects of the subject disclosure, systems and methods are provided for stabilizing portions of bone, for example, by reducing the thickness of plates without sacrificing the strength of the plates. In some aspects, a plate may incorporate a "keel" feature along its bottom surface. The keel may provide additional strength to the plate structure, thereby allowing the thickness to be reduced. In some aspects, fasteners may be used to attach the plate to bone portions for increased stabilization. The plate may be used with joint fusion procedures in which there are limited soft tissue coverage and where there are high levels of torsion and 3-point bends. For example, the plate can be used for small/medium joint fusion procedures, including fusions of the joint(s) of the hand, the foot, the ankle, the knee, the wrist, the shoulder, two bone portions of a fractured bone, two bone portions of a cut bone, or other natural or artificial joints. A thinner plate can be less prominent and create less soft tissue irritation, which may be particularly useful in joints with limited soft tissue coverage. The plate may control rotation, facilitate linear compression, and/or minimize soft tissue irritation.

FIGS. 1A, 1B, and 1C illustrate an example of a bone plate system 10, in accordance with various aspects of the subject disclosure. FIG. 1A shows a side view of bone plate system 10, FIG. 1B shows a top view of bone plate system 10, and FIG. 1C shows a front view of bone plate system 10. Bone plate system 10 may comprise plate 12 and keel 14. Plate 12, having a bone engaging surface (e.g., the bottom side of plate 12 as shown in FIGS. 1A and 1C), may be fastened to two bone portions having a joint line therebetween, for example, for fusing the bone portions. Keel 14 may project from the bone engaging surface and extend into the bone portions and span the joint line when plate 12 is fastened to the bone portions. Plate 12 may comprise one or more holes 16 such that the one or more holes 16 may receive one or more fasteners therethrough for fastening plate 12 to the bone portions. The one or more holes 16 may be counter-sunk (e.g., such that heads of fasteners may lie below a surface of plate 12). In some aspects, the one or more fasteners may also span the joint line.

In some aspects, plate 12 and keel 14 may be integrally formed. In some aspects, plate 12 and keel 14 may be separately formed. In some aspects, plate 12 may be substantially orthogonally coupled to keel 14 (e.g., as seen in a side view of bone plate system 10 in FIG. 1C). Plate 12 may be curved or flat. At least one of plate 12 and keel 14 may comprise at least one of steel and titanium. In some aspects, keel 14 may comprise an ingrowth material to achieve further stability and encourage bone growth. Keel 14 may comprise porous metal. For example, keel may comprise at least one of trabecular metal (e.g., tantalum spray on a styrofoam substrate) and biofoam (e.g., titanium on a similar substrate). Keel 14 may comprise any materials known to those of skill in the art to form an osteointegrative surface thereon (e.g., surface for bone integration).

Keel 14 may increase the tortional stiffness as compared with traditional plates. The inclusion of keel 14 in bone plate system 10 may allow plate 12 to have a thinner profile. In some aspects, the average length of plate 12 may be greater than the average width of plate 12, which may be greater than the average thickness of plate 12. Thus, the inclusion of keel 14 in bone plate system 10 may reduce a ratio between the average thickness of plate 12 to an average width of plate 12 compared to traditional plates without keel 14. In some aspects, a ratio of an average thickness of plate 12 to an average width of plate 12 is less than or equal to about 0.11. In some aspects, a ratio of an average thickness of plate 12 to an average width of plate 12 is less than or equal to about 0.10. In some aspects, a ratio of an average thickness of plate 12 to an average width of plate 12 is less than or equal to about 0.09. In some aspects, a ratio of an average thickness of plate 12 to an average width of plate 12 is less than or equal to about 0.08. In some aspects, a ratio of an average thickness of plate 12 to an average width of plate 12 is less than or equal to about 0.07. In some aspects, a ratio of an average thickness of plate 12 to an average width of plate 12 is less than or equal to about 0.06. In some aspects, a ratio of an average thickness of plate 12 to an average width of plate 12 is less than or equal to about 0.05. In some aspects, a ratio of an average thickness of plate 12 to an average width of plate 12 is less than or equal to about 0.04. In some aspects, a ratio of an average thickness of plate 12 to an average width of plate 12 is less than or equal to about 0.03.

Figure 2A:
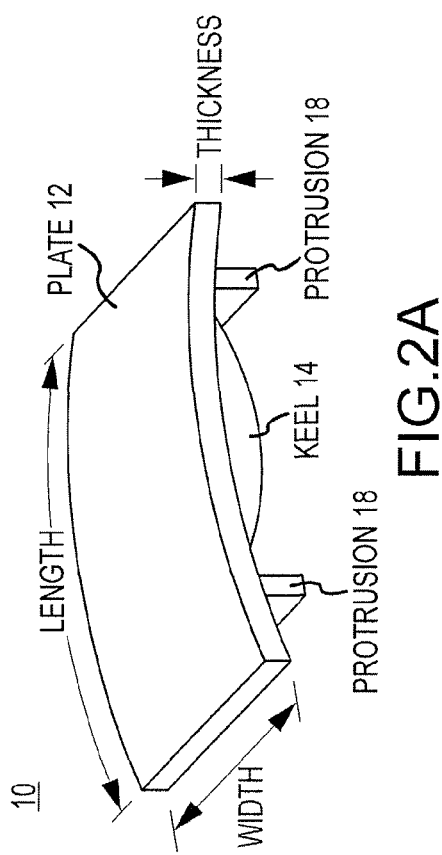
Figure 2B:
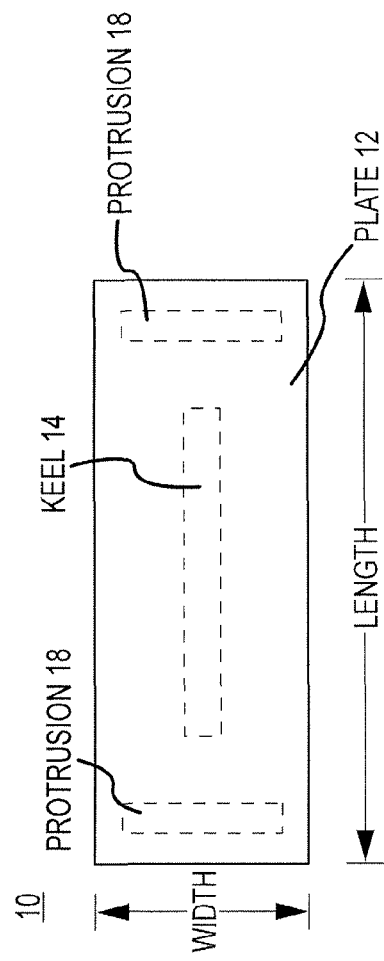

FIGS. 2A, 2B, and 2C illustrate an example of bone plate system 10 with one or more protrusions 18, in accordance with various aspects of the subject disclosure. Bone plate system 10, as shown here, may further comprise one or more protrusions 18 protruding from the bone engaging surface of plate 12. The one or more protrusions 18 may extend into at least one of the bone portions when plate 12 is fastened to the bone portions. The one or more protrusions 18 may provide further stability to bone plate system 12. In some aspects, the one or more protrusions 18 may reinforce plate 12. In some aspects, the one or more protrusions 18 may maintain alignment for osteotomies. In some aspects, plate 12 and the one or more protrusions 18 may be integrally formed. In some aspects, plate 12 and the one or more protrusions 18 may be separately formed.

Figure 3A:
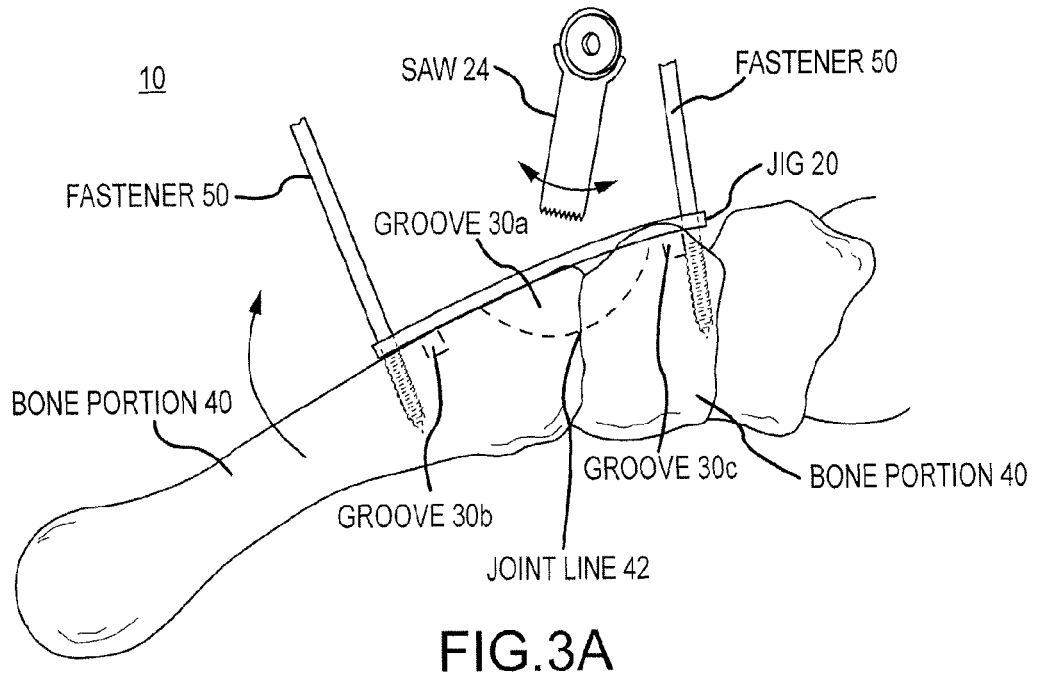
FIGS. 3A and 3B illustrate an example of a jig used for fastening a plate to bone portions, in accordance with various aspects of the subject disclosure.
Figure 3B:
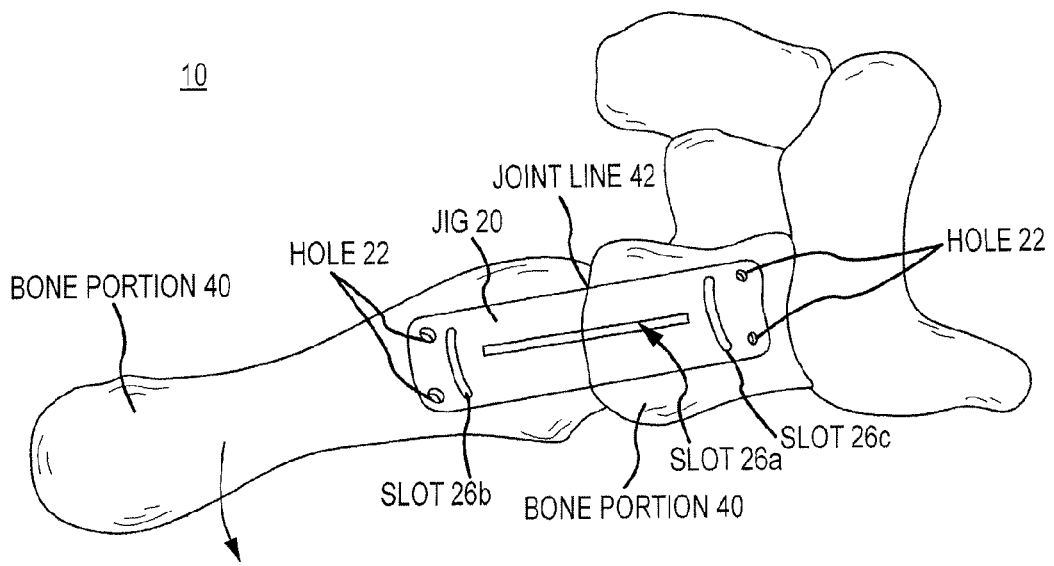

FIGS. 3A and 3B illustrate an example of a jig 20 used for fastening plate 12 to bone portions 40, in accordance with various aspects of the subject disclosure. FIG. 3A shows a side view of bone plate system 10, and FIG. 3B shows a top view of bone plate system 10. Bone plate system 10 may further comprise jig 20, saw 24, and one or more k wires 28. In some aspects, jig 20 may be used as a guide for saw 24 to cut a groove into bone portions 40 such that plate 12 may be fastened to bone portions 40 with keel 14 fitting substantially within the groove.

In some aspects, bone portions 40 may be of a same bone or of different bones. Bone portions 40 may define a joint therebetween. The joint may be a natural joint, such as between two natural bones, or the joint may be an artificial joint, such as between two bone portions of the same bone separated by a fracture or osteotomy. Joint line 42 separates bone portions 40. For example, joint line 42 may be a fracture or osteotomy line.

Jig 20 may comprise one or more holes 22. In some aspects, jig 20 may be fastened to bone portions 40 using fasteners 50. Holes 22 may receive fasteners 50 therethrough for fastening and securing jig 20 to bone portions 40. For example, holes may be drilled through holes 22 to form channels in bone portions 40 such that fasteners 50 may be inserted through holes 22 into the channels for fastening jig 20 to bone portions 40. Fasteners 50 may comprise k wires, screws, nails, or other suitable fasteners known to those of skill in the art.

Jig 20 may also comprise one or more slots 26 (e.g., as shown by slot 26a, 26b, and 26c). Slots 26 may permit cutting of bone through a respective slot. For example, saw 24 may be used to cut bone through slots 26 to form grooves 30 (e.g., as shown by groove 30a, 30b, and 30c). In some aspects, slots 26 may span joint line 42 (e.g., slot 26a) when jig 20 is fastened to bone portions 40.

Figure 4A:
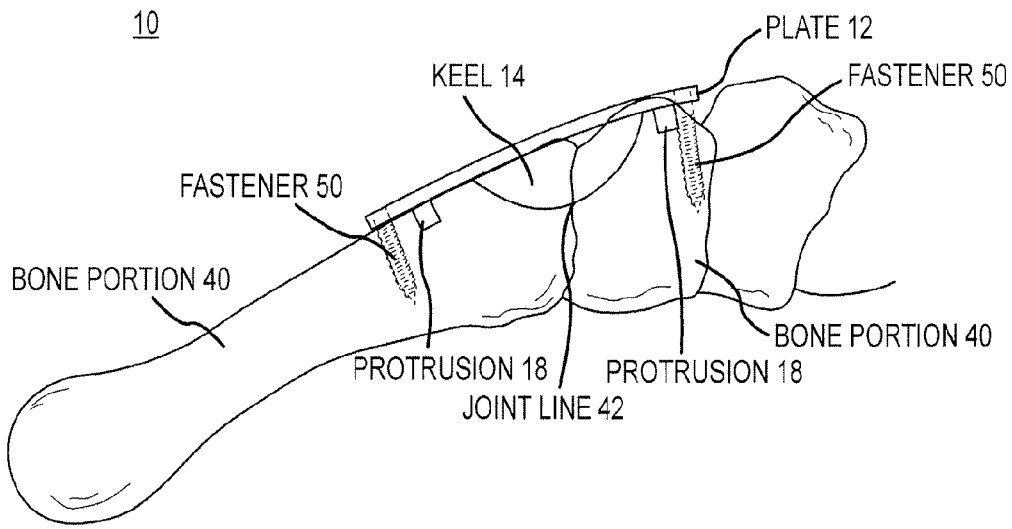
FIGS. 4A and 4B illustrate an example of a bone plate system with a plate fastened to bone portions, in accordance with various aspects of the subject disclosure.
Figure 4B:
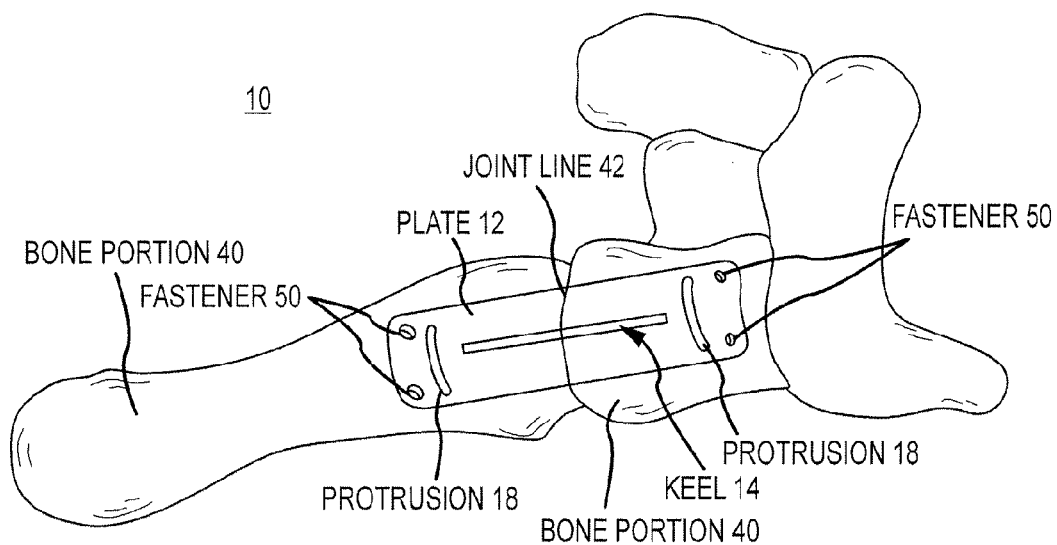

FIGS. 4A and 4B illustrate an example of bone plate system 10 with plate 12 fastened to bone portions 40, in accordance with various aspects of the subject disclosure. FIG. 4A shows a side view of bone plate system 10, and FIG. 4B shows a top view of bone plate system 10. Plate 12 may be fastened to bone portions 40 such that keel 14 fits substantially within groove 30a of FIG. 3A. In some aspects, plate 12 may be fastened to bone portions 40 such that protrusions 18 may fit substantially within grooves 30b and 30c. Keel 14 may reduce rotational, torsional and/or translational forces acting on bone portions 40.

Figure 5A:
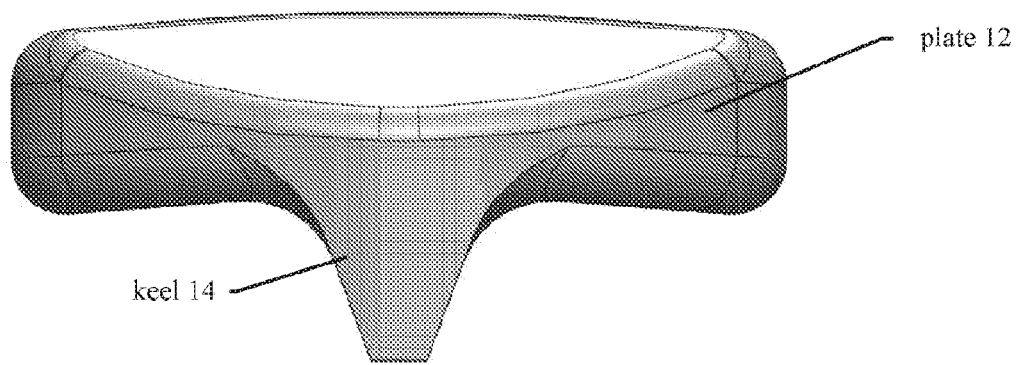
FIGS. 5A, 5B, 5C, 5D, 5E, 5F, 5G, 5H, 5I, 5J, 5K, and 5L illustrate various configurations of a plate and a keel, in accordance with various aspects of the subject disclosure.
Figure 5B:
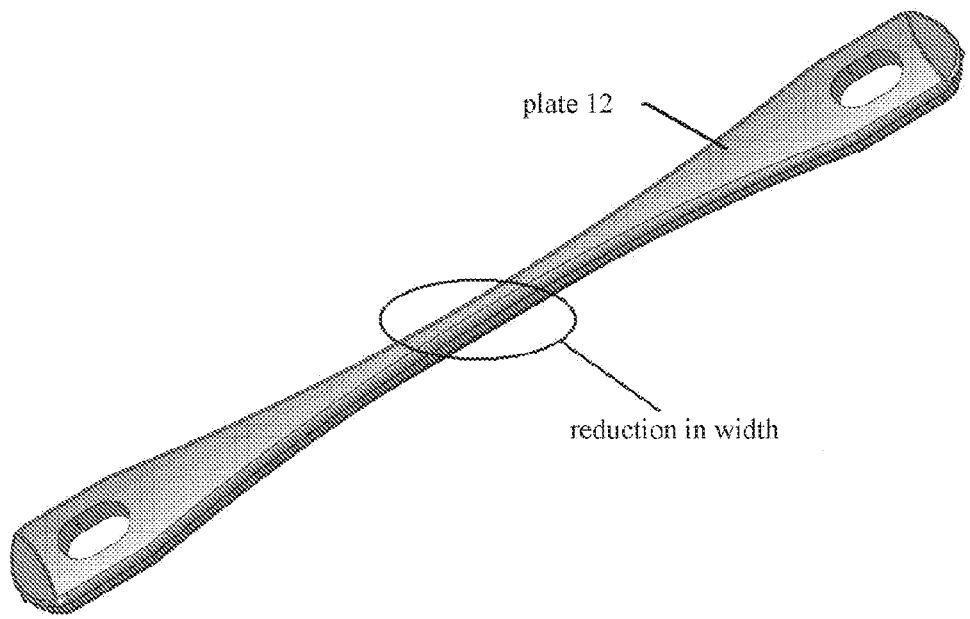
Figure 5C:
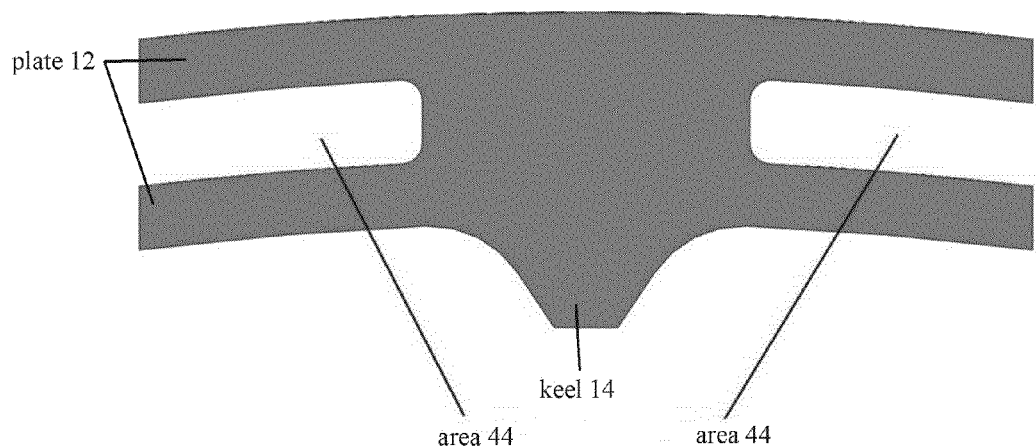
Figure 5D:
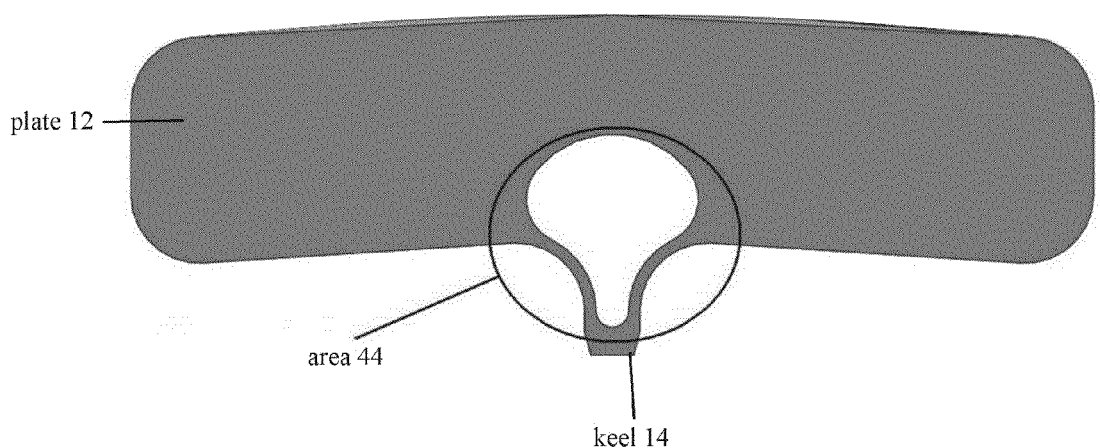
Figure 5E:
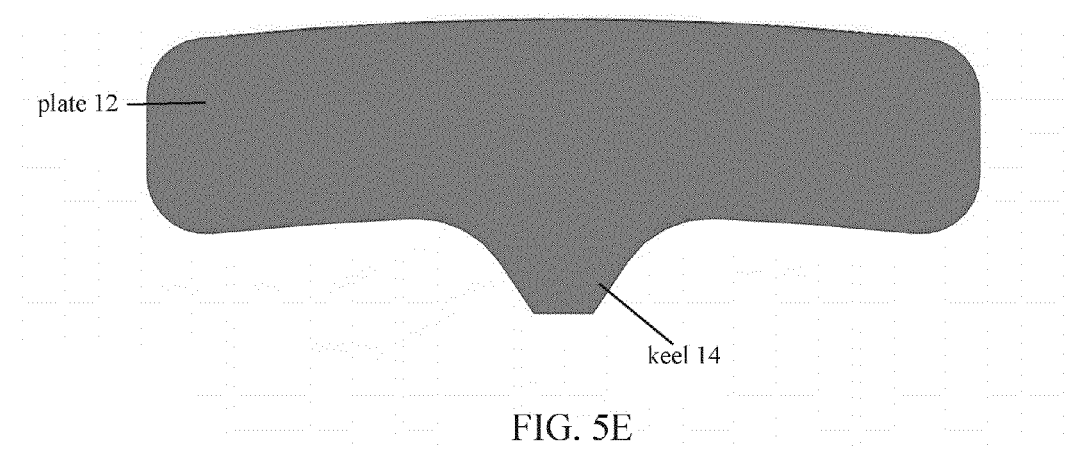
Figure 5F:
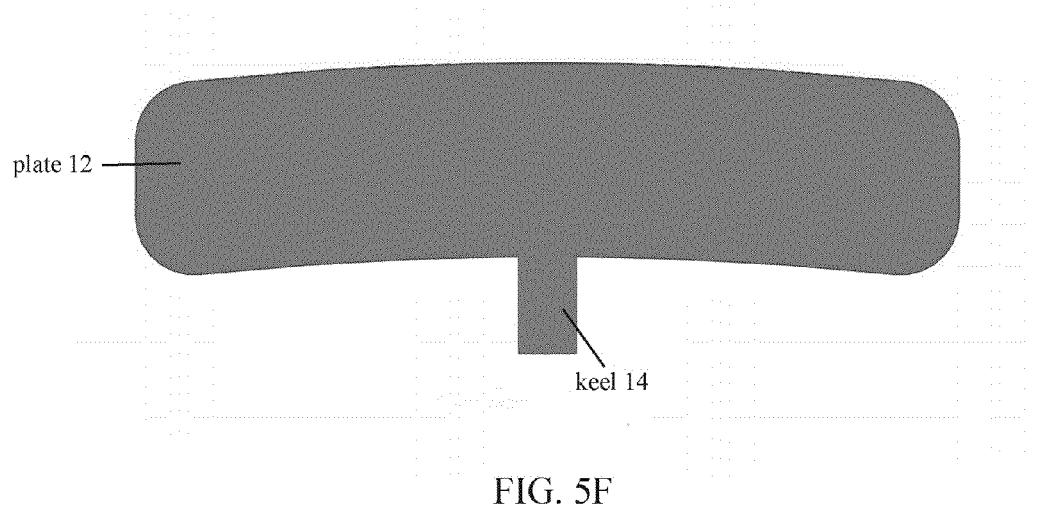
Figure 5G:
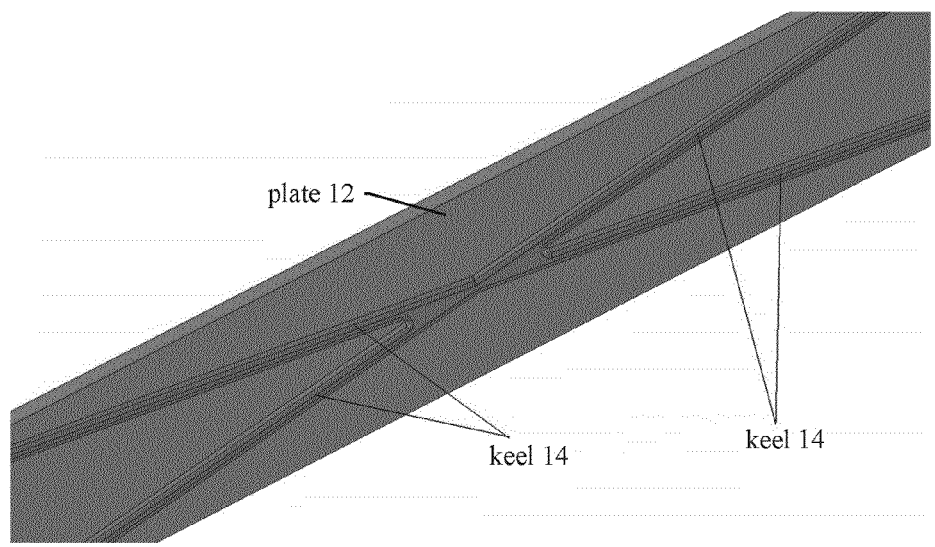

FIGS. 5A, 5B, 5C, 5D, 5E, 5F, 5G, 5H, 5I, 5J, 5K, and 5L illustrate various configurations of plate 12 and keel 14, in accordance with various aspects of the subject disclosure. For example, FIG. 5B illustrates that with the addition of keel 14 (not shown), the width of plate 12 may be reduced compared with traditional plates. FIGS. 5C, 5D, 5E, and 5F show a front view of plate 12 with keel 14. FIGS. 5C and 5D illustrate that with the addition of keel 14, plate 12 may be reduced as shown by hollow areas 44. FIG. 5G illustrates an example of keel 14 comprising an "X" configuration, in accordance with some aspects of the subject disclosure.

Figure 5I:
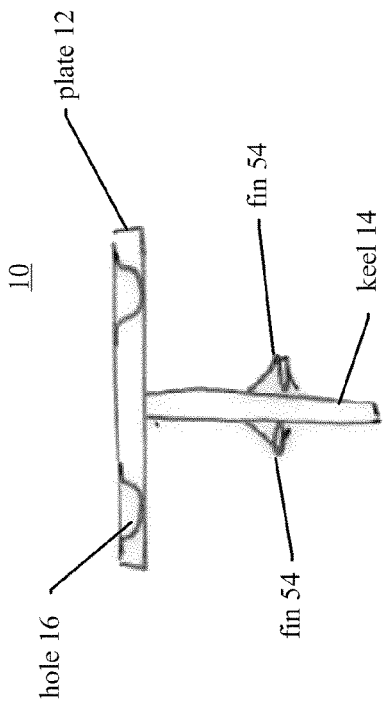
Figure 5H:
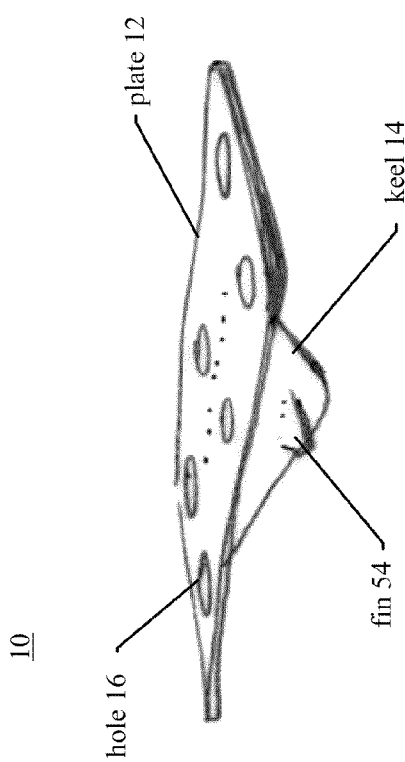
Figure 5J:
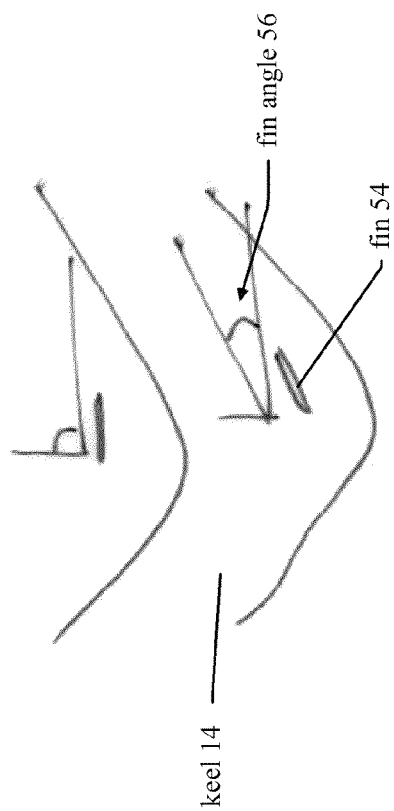

FIGS. 5H, 5I, and 5J illustrate an example of bone plate system 10 with fin 54 coupled to keel 14, in accordance with various aspects of the subject disclosure. FIG. 5H shows a general view of bone plate system 10. FIG. 5I shows a front view of bone plate system 10, and FIG. 5J shows a side view of keel 14 and fin 54. Fin 54 may provide further stability plate 12 when plate 12 is fastened to one or more bone portions. Furthermore, having fin 54 may result in bone portions becoming aligned with each other and compressing against each other when plate 12 is being fastened to the bone portions. Fin 54 may project from keel 14 and have a fin angle 56 with respect to plate 12. For example, a long axis of fin 54 and a long axis of plate 12 may be substantially non-parallel. In some aspects, fin 54 and keel 14 may be integrally formed. In some aspects, fin 54 may comprise at least one of steel and titanium. In some aspects, fin 54 may comprise porous metal. For example, fin 54 may comprise at least one of trabecular metal and biofoam. Fin 54 may be substantially orthogonally coupled to keel 14.

Figure 5K:
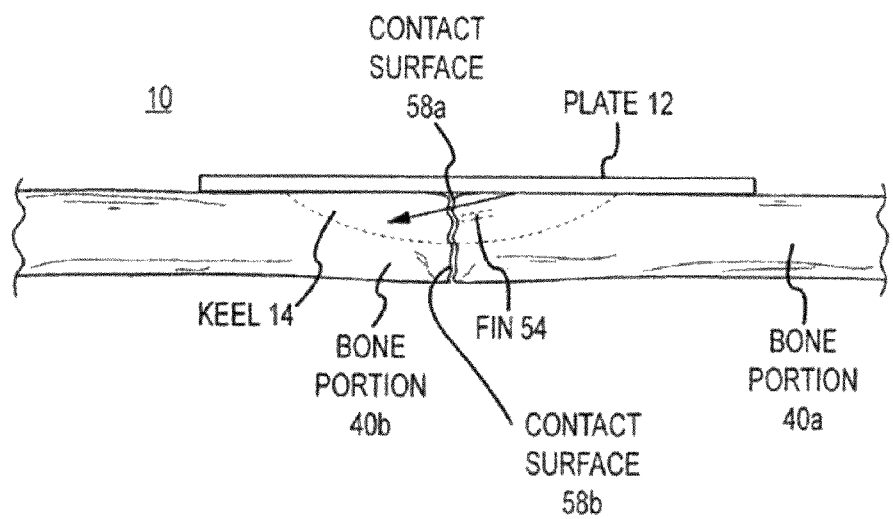
Figure 5L:
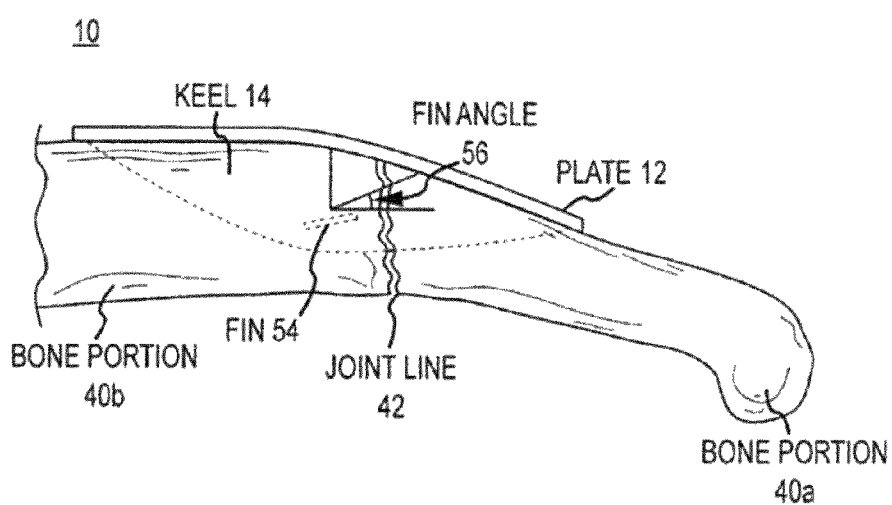

FIGS. 5K and 5L illustrate bone plate system 10 with plate 12, having fin 54 coupled to keel 14, fastened to bone portions 40 (e.g., bone portions 40a and 40b), in accordance with various aspects of the subject disclosure. Plate 12 may first be fastened to bone portion 40a such that a first portion of keel 14 may fit substantially within a groove of bone portion 40a. In some aspects, fin 54 may project from a portion of keel 14 that is within a groove of bone portion 40a, as shown in FIG. 5K. In some aspects, fin 54 may project from a portion of keel 14 that is not within a groove of bone portion 40a as shown in FIG. 5L. In this way, as plate 12 is fastened to bone portion 40b, keel 14 may span joint line 42 and fin 54 (a) may be inserted through contact surface 58b of bone portion 40b, and thereafter (b) may be progressively advanced into bone portion 40b such that (i) contact surface 58a of bone portion 40a makes contact with contact surface 58b of bone portion 40b and (ii) a second portion of keel 14 fits substantially within a groove of bone portion 40b. In some aspects, fin 54 may be inserted and advanced into a cancellous portion of bone portions 40.

Fin 54 may act to provide alignment between bone portions 40 and/or compression of bone portions 40 against each other. For example, as (a) plate 12 is fastened to bone portions 40 and (b) after contact surface 58a of bone portion 40a makes contact with contact surface 58b of bone portion 40b, fin 54 is progressively advanced into bone portion 40b such that bone portions 40 become aligned with each other and progressively compress against each other. In another example, as (a) plate 12 is fastened to bone portions 40 and (b) fin 54 is progressively advanced into bone portion 40b, fin 54 moves in bone portion 40b in a direction away from contact surface 58b of bone portion 40b and away from plate 12. In some aspects, adjusting fin angle 54 may correspondingly allow fin 54 to move farther in a direction either away or towards plate 12 as fin 54 is advanced into bone portion 40b.

Figure 6A:
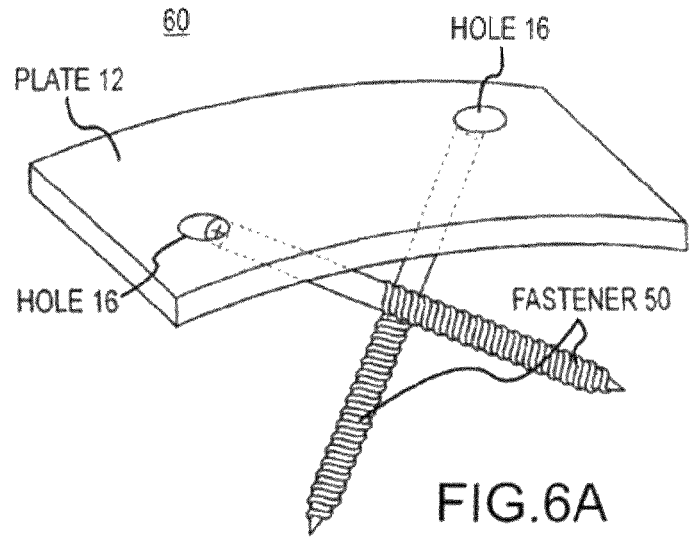
FIGS. 6A, 6B, and 6C illustrate an example of a bone plate system utilizing fasteners for stabilizing bone portions, in accordance with various aspects of the subject disclosure.
Figure 6B:
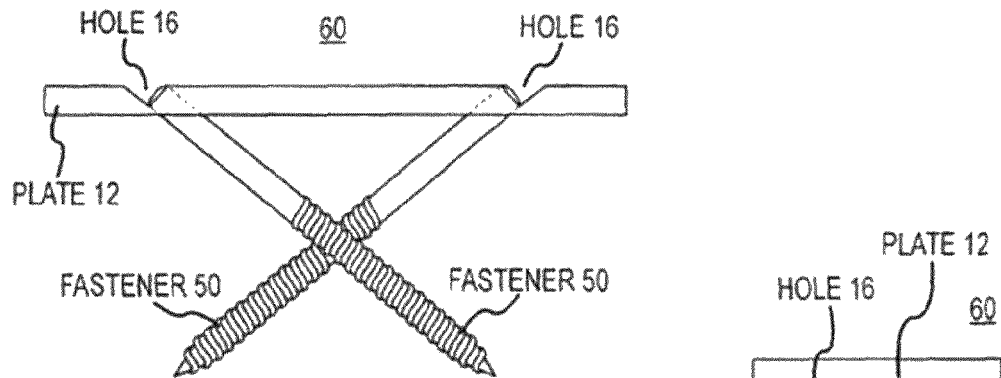
Figure 6C:
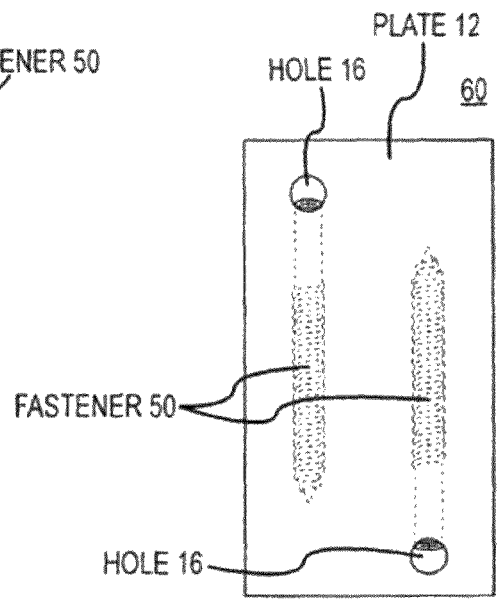

FIGS. 6A, 6B, and 6C illustrate an example of bone plate system 60 utilizing fasteners 50 for stabilizing bone portions, in accordance with various aspects of the subject disclosure. FIG. 6A shows a side view of bone plate system 60, FIG. 6B shows a top view of bone plate system 60, and FIG. 6C shows a front view of bone plate system 60. Bone plate system 60 may comprise plate 12 and one or more fasteners 50. Plate 12 may comprise one or more holes 16. Fasteners 50 may extend through holes 16 and fasten plate 12 to bone portions. Fasteners 50 may comprise k wires, screws, nails, or other suitable fasteners known to those of skill in the art. Fasteners 50 may be made of at least one of titanium, cobalt, and other suitable materials known to those of skill in the art.

Figure 7A:
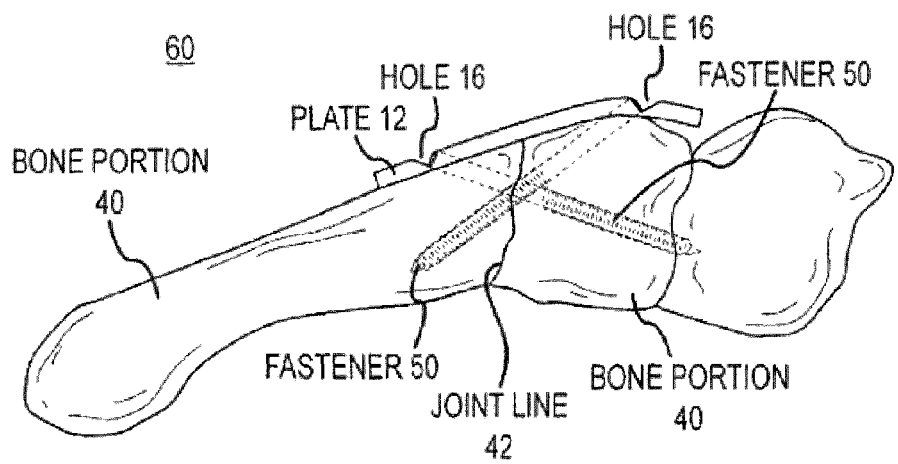
FIGS. 7A and 7B illustrate an example of a bone plate system with a plate fastened to bone portions, in accordance with various aspects of the subject disclosure.
Figure 7B:
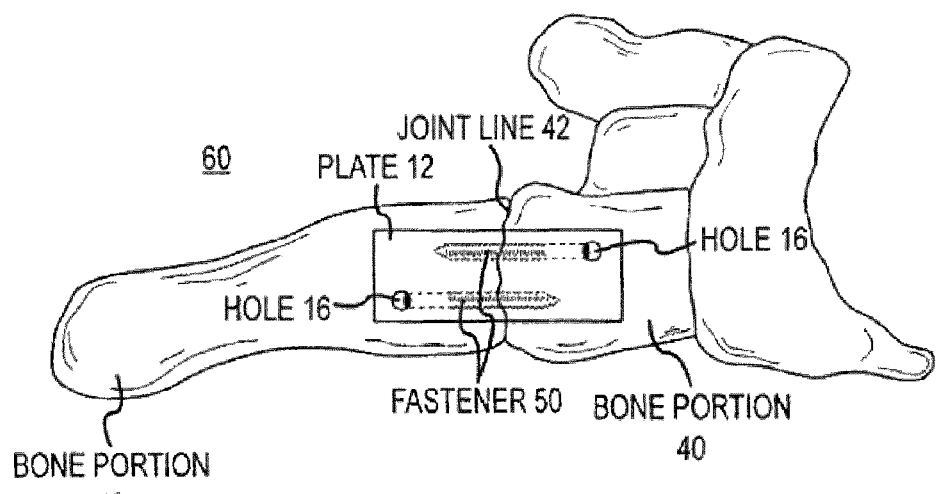

FIGS. 7A and 7B illustrate an example of bone plate system 60 with plate 12 fastened to bone portions 40, in accordance with various aspects of the subject disclosure. FIG. 7A shows a side view of bone plate system 60, and FIG. 7B shows a top view of bone plate system 60. Plate 12 may make contact with bone portions 40 having a joint line 42 therebetween. Bone may be drilled through locations corresponding to holes 16 to form channels into bone portions 40. As shown, fasteners 50 may be inserted through holes 16 into the channels and fasten plate 12 to bone portions 40. A fastener 50 may be inserted at an angle such that when fastener 50 extends through a hole 16 and fastens plate 12 to bone portions 40, fastener 50 may span joint line 42. Hole 16 may be countersunk such that a head of fastener 50 may lie below a surface of plate 12. For example, hole 16 may comprise an indentation into plate 12 such that when fastener 50 is angled and inserted through hole 16, the non-bone engaging end of fastener 50 does not protrude out of the non-bone engaging surface of plate 12.

Figure 8A:
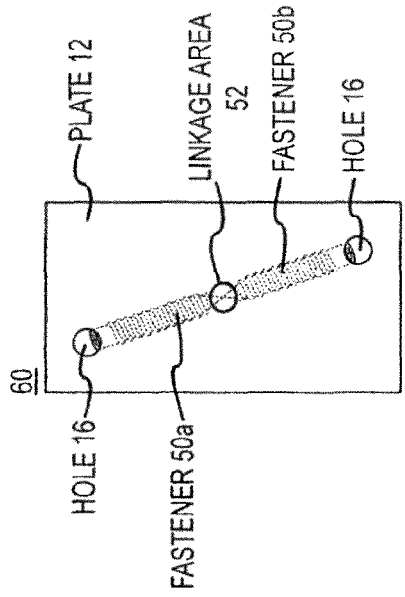
FIGS. 8A, 8B, 8C, and 8D illustrate various configurations of a bone plate system, in accordance with various aspects of the subject disclosure.
Figure 8B:
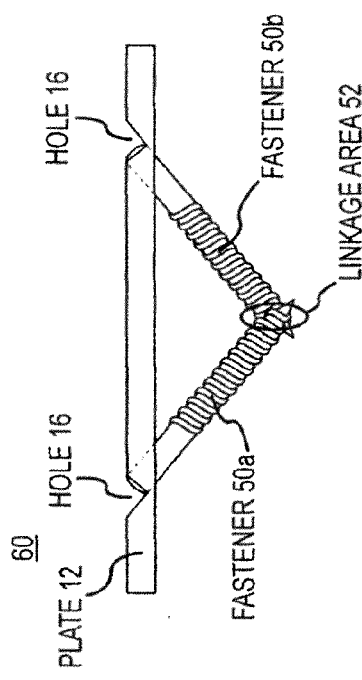
Figure 8C:
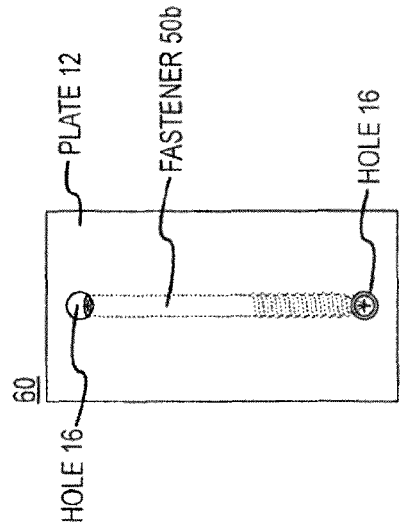
Figure 8D:
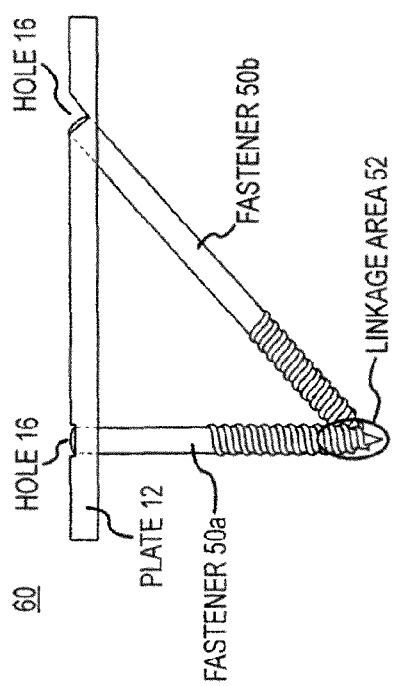

FIGS. 8A, 8B, 8C, and 8D illustrate various configurations of bone plate system 60, in accordance with various aspects of the subject disclosure. In some aspects, a portion of a first fastener 50a may be coupled to a portion of second fastener 50b when both fasteners are inserted into bone portions 40. For example, first fastener 50a may be inserted through a first hole 16 into a first channel and fasten plate 12 to bone portions 40. Second fastener 50b may be inserted through a second hole 16 into a second channel such that a portion of second fastener 50b is coupled to a portion of first fastener 50a at linkage area 52. FIGS. 8A and 8B show side views of bone plate system 60 while FIGS. 8C and 8D show corresponding top views. The coupling of fasteners 50 when both fasteners are inserted into bone portions 40 may provide further resistance against any possible loosening of plate 12 and/or fasteners 50 from bone portions 50. For example, crossed fasteners 50 may capture wedges of bone to resist pullout of fasteners 50. In one example, fastener 50b may be pushed against fastener 50a at linkage area 52 such that fastener 50a provides a counter force against fastener 50b. In this way, fastener 50a may act as a spring, keeping both fasteners 50 coupled together.

Figure 9A:
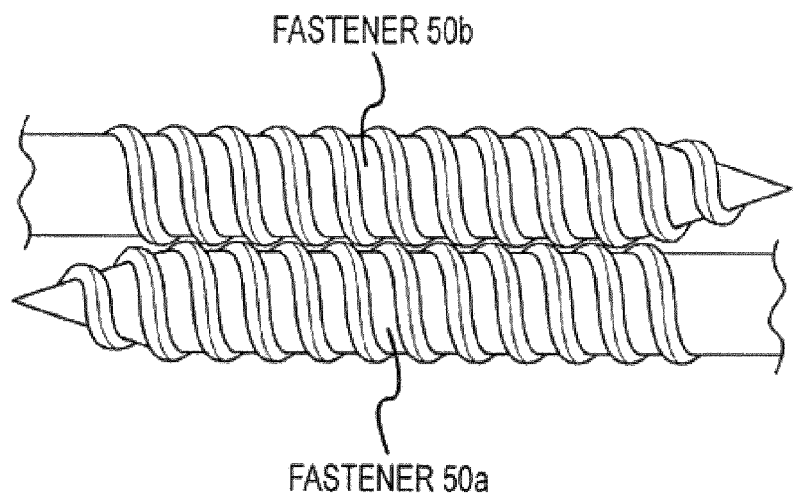
FIGS. 9A and 9B illustrate an example of fasteners of a bone plate system interdigitating with each other, in accordance with various aspects of the subject disclosure.
Figure 9B:
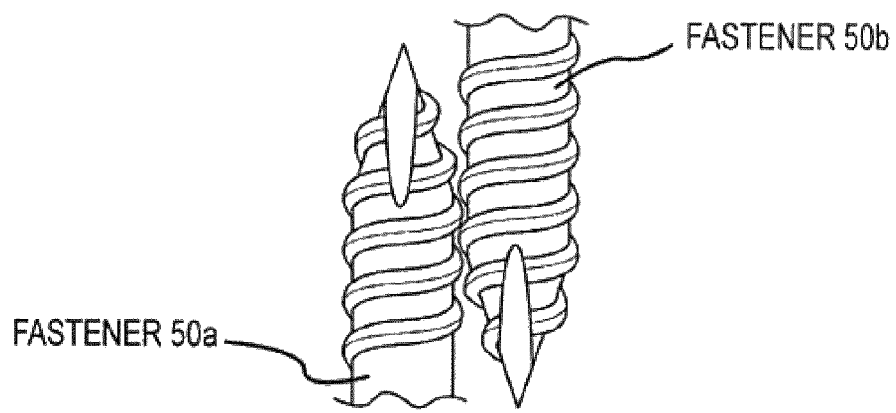

In some aspects, the portion of second fastener 50b may be coupled to the portion of first fastener 50a through at least one of interdigitation, locking, adhesion, and fusion. In one example, first fastener 50a and second fastener 50b may be made of materials different in hardness from one another. In this way, as second fastener 50b is inserted through second hole 16 such that the portion of second fastener 50b is coupled to the portion of first fastener 50a, the respective coupling portions of fasteners 50 will fuse and/or lock with each other because the fastener with a lower measure of hardness will give way to the other. For example, first fastener 50a and second fastener 50b may be made of metals of dissimilar densities. These metals may be biocompatible, and interdigitation of these metals may allow for cold welding. In some aspects, portions of fasteners 50a and 50b (e.g., at a tip or other portions that couple to the other fastener) may include adhesive materials such that when the portions make contact, the portions adhere to each other. FIGS. 9A and 9B illustrate an example of fasteners 50 of bone plate system 50 interdigitating with each other, in accordance with various aspects of the subject disclosure. Thus, in some aspects, if fasteners 50 comprise screws, the threads of fastener 50a may be oriented to interdigitate with the threads of fastener 50b such that fastener 50b is coupled to fastener 50a (e.g., mechanical interference exists between respective screw threads of fasteners 50). In such a case, fasteners 50 may be formed such that their respective threads are oriented correctly when taking into account the angle of insertion into bone portions 40.

Figure 10A:
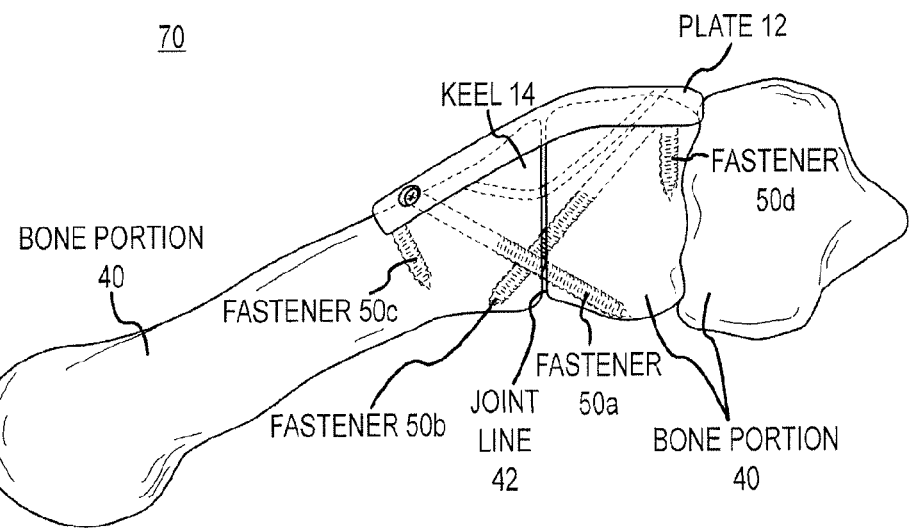
FIGS. 10A and 10B illustrate an example of a bone plate system, in accordance with various aspects of the subject disclosure.
Figure 10B:
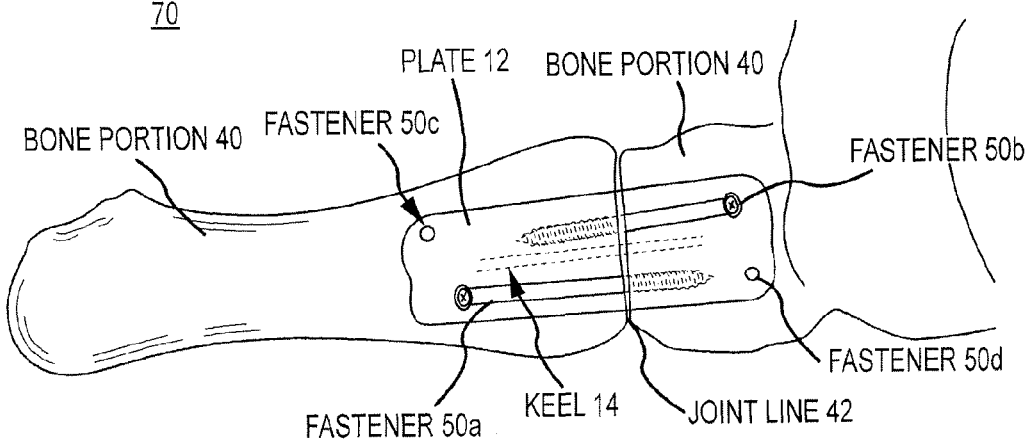

FIGS. 10A and 10B illustrate an example of bone plate system 70, in accordance with various aspects of the subject disclosure. FIG. 10A shows a side view of bone plate system 70, and FIG. 10B shows a top view of bone plate system 70. Bone plate system 70 may comprise plate 12, keel 14, and one or more fasteners 50 (e.g., as shown by fasteners 50a, 50b, 50c, and 50d). As shown, plate 12 may include keel 14 in addition to having fasteners 50 fasten plate 12 to bone portions 40. Fasteners 50a and 50b may be inserted into bone portions 40 such that they span joint line 42, while fasteners 50c and 50d do not span joint line 42. In some aspects, bone plate system 70 may further comprise one or more protrusions 18 of FIGS. 4A and 4B.

Figure 11B:
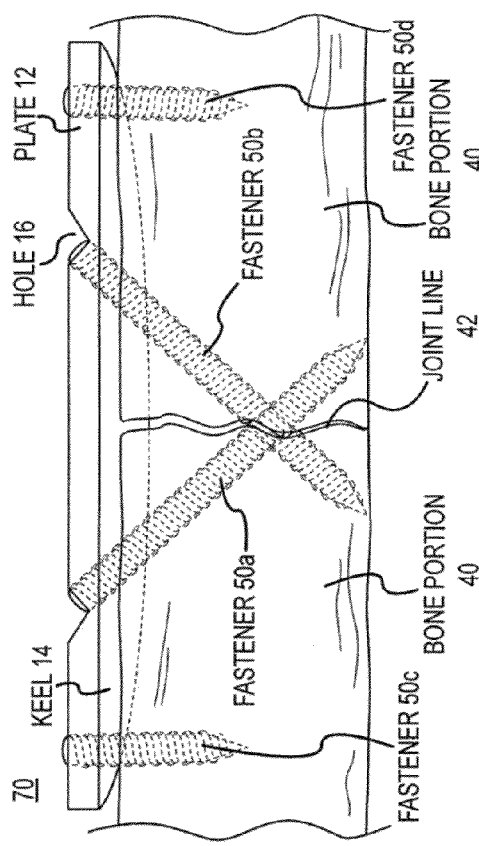
Figure 11D:
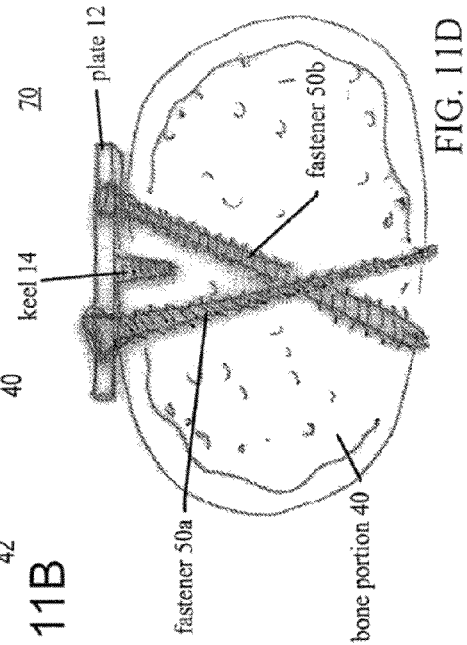
Figure 11C:
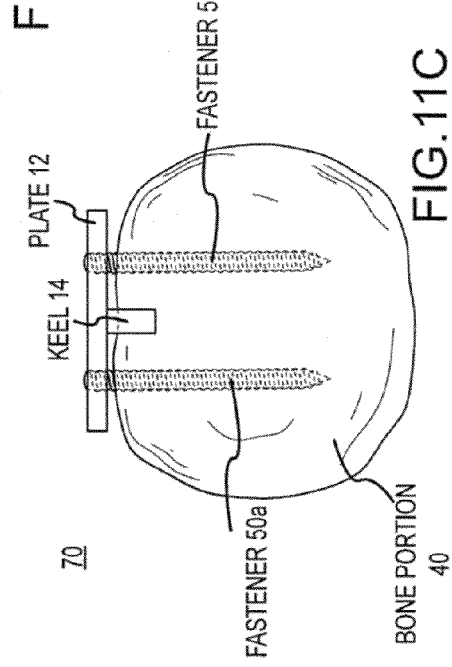

FIGS. 11A, 11B, 11C, and 11D illustrate various configurations of bone plate system 70, in accordance with various aspects of the subject disclosure. FIG. 11A illustrates an example of bone plate system 70 comprising plate 12, keel 14, and fasteners 50 coupled to each other at linkage area 52. FIGS. 11B, 11C, and 11D illustrate examples of bone plate system 70 where fasteners 50 span joint line 42 and may or may not couple with one another.

Figure 12A:
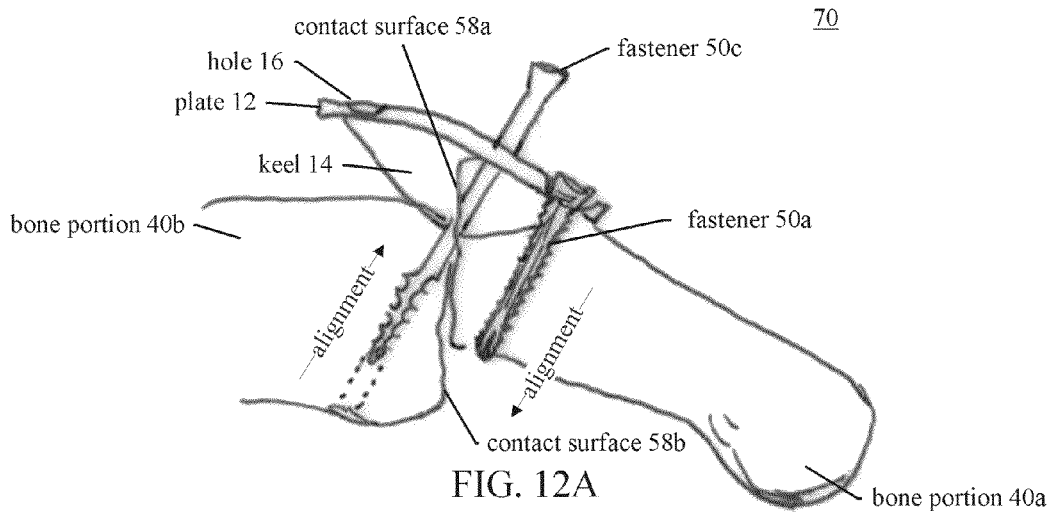
FIGS. 12A, 12B, and 12C illustrate examples of a bone plate system used for stabilizing and compressing bone portions, in accordance with various aspects of the subject disclosure.
Figure 12B:
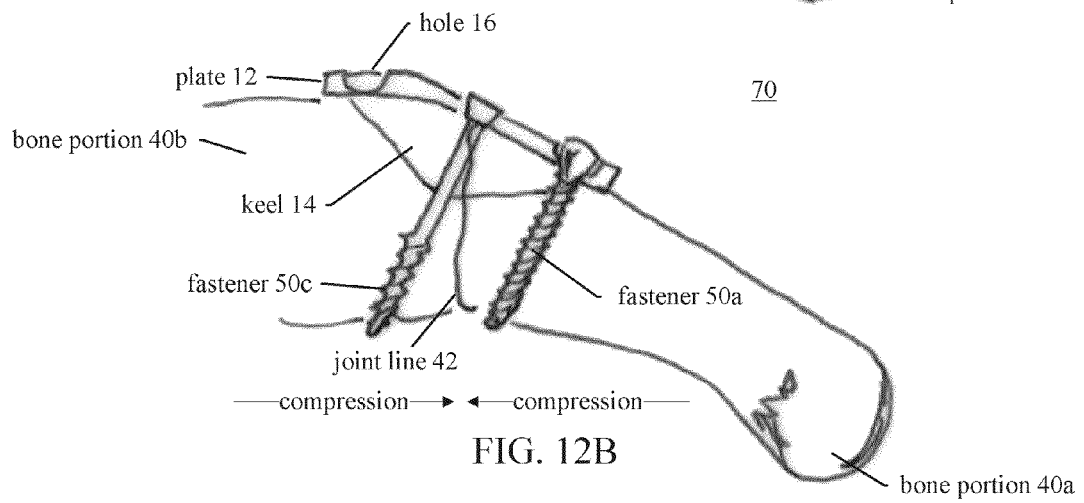
Figure 12C:
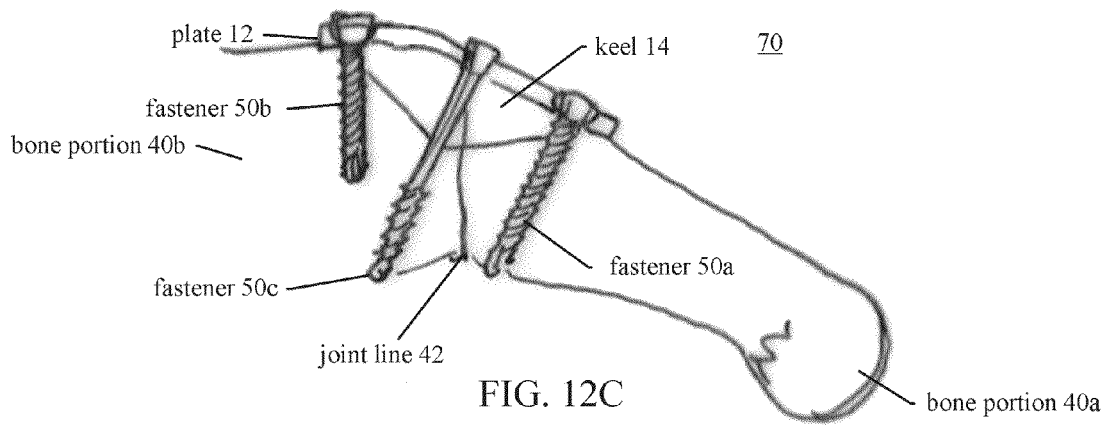

FIGS. 12A, 12B, and 12C illustrate examples of bone plate system 70 used for stabilizing and compressing bone portions 40, in accordance with various aspects of the subject disclosure. In some aspects, plate 12 may be affixed to bone portion 40a as shown in FIG. 12A. For example, fastener 50a may be used to fasten plate 12 to bone portion 40a. Fastener 50c (e.g., a compression screw) may be inserted through a hole of plate 12 into bone portion 40a, and thereafter through contact surface 58a of bone portion 40a, and thereafter through contact surface 58b of bone portion 40b and into bone portion 40b, such that when fastener 50c is advanced, contact surface 58a of bone portion 40a makes contact with contact surface 58b of bone portion 40b. Fastener 50c may be progressively advanced such that bone portions 40 become aligned with each other and progressively compress against each other, as shown in FIGS. 12A and 12B. Fastener 50b may be inserted through another hole of plate 12 into bone portion 40b in order to further fasten plate 12 onto bone portions 40, as shown in FIG. 12C. In some aspects, fastener 50b may span joint line 42 when inserted into bone portion 40b. For example, fastener 50b may be inserted into bone portion 40b, and thereafter through contact surface 58b of bone portion 40b, and thereafter through contact surface 58a of bone portion 40a and into bone portion 40a.

Figure 14A:
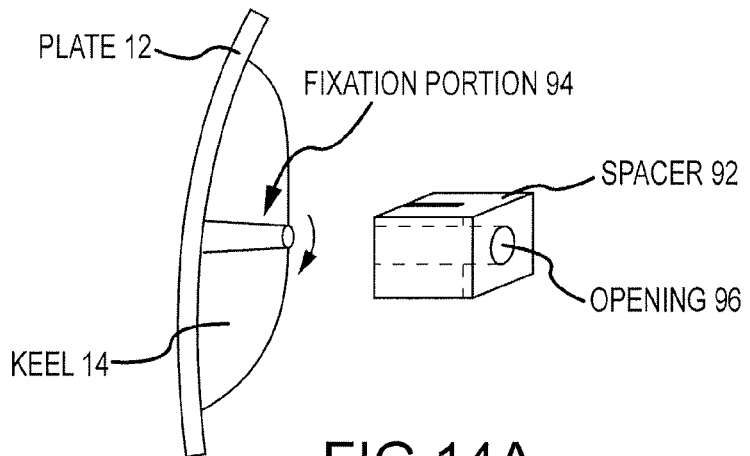
FIGS. 14A, 14B, and 14C illustrate a spacer in detail, in accordance with various aspects of the subject disclosure.
Figure 14B:
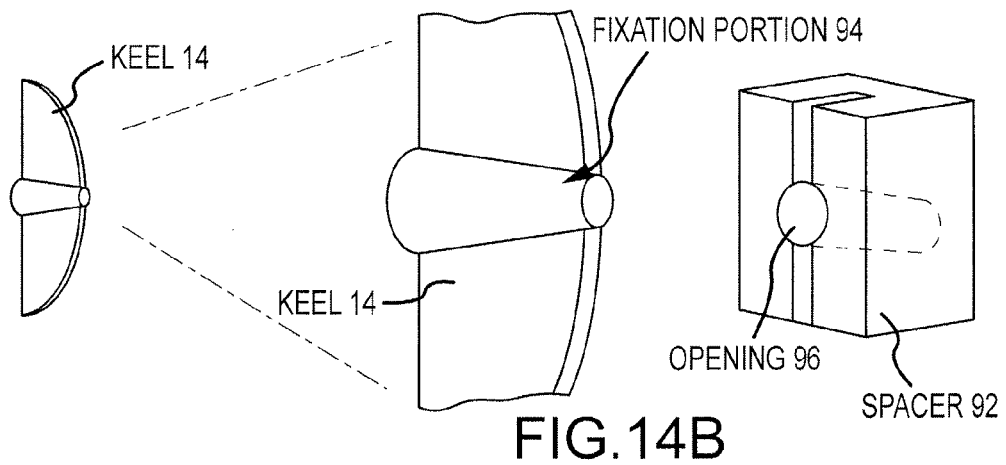
Figure 14C:
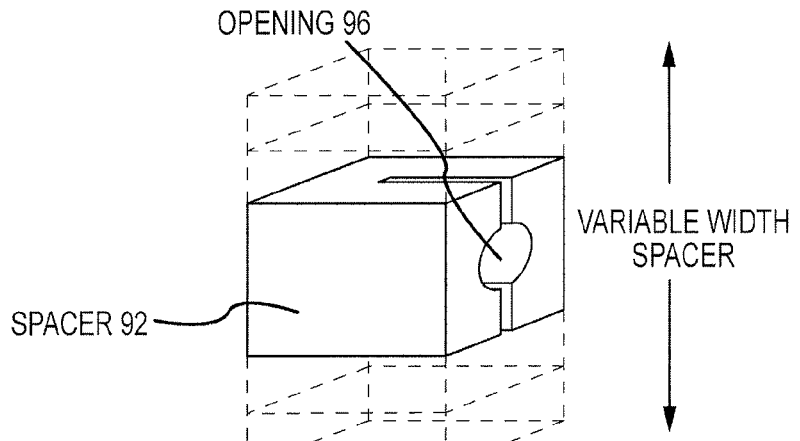

FIGS. 13A and 13B illustrate examples of bone plate system 90, in accordance with various aspects of the subject disclosure. Bone plate system 90 may comprise plate 12, keel 14, and spacer 92 in or on at least one of plate 12 and keel 14. Spacer 92 may be used additionally with the bone plate systems as described herein for osteotomies or other suitable uses known to those of skill in the art. For example, spacer 92 may reside between bone portions when plate 12 is fastened to the bone portions. FIGS. 14A, 14B, and 14C illustrate spacer 92 in detail, in accordance with various aspects of the subject disclosure. In some aspects, at least one of plate 12 and keel 14 comprises fixation portion 94 (e.g., morse taper) that engages spacer 92. Fixation portion 94 may fit substantially within a correspondingly sized opening 96 in spacer 92. Keel 14 may control and/or prevent rotation of spacer 92. In some aspects, spacer 92 may comprise at least one of a notch and a thread engaging fixation portion 94. In one example, fixation portion 94 may be a screw, pin, and/or protrusion, and spacer 92 may have an opening 96 that engages fixation portion 94 with threads, notches, and/or other suitable means. In some aspects, spacer 92 friction fits into or onto at least one of plate 12 and keel 14. In some aspects, spacer 92 is reversibly coupled to at least one of plate 12 and keel 14. Spacer 92 may have a variable width suitable for different spacing needed between bone portions. In one example, various spacers 92, each corresponding to a different width, may be used depending on a spacing needed for application of bone plate system 90. Interchangeability of various spacers 92 may allow for decreased plate inventory.

In some aspects, at least one of (a) plate 12 and keel 14, (b) keel 14 and spacer 92, and (c) plate 12 and spacer 92 are integrally formed. In some aspects, at least one of (a) plate 12 and keel 14, (b) keel 14 and spacer 92, and (c) plate 12 and spacer 92 are substantially orthogonally coupled to each other. In some aspects, at least one of plate 12, keel 14, and spacer 92 comprise at least one of steel and titanium. In some aspects, at least one of keel 14 and spacer 92 comprises porous metal.

Figure 15A:
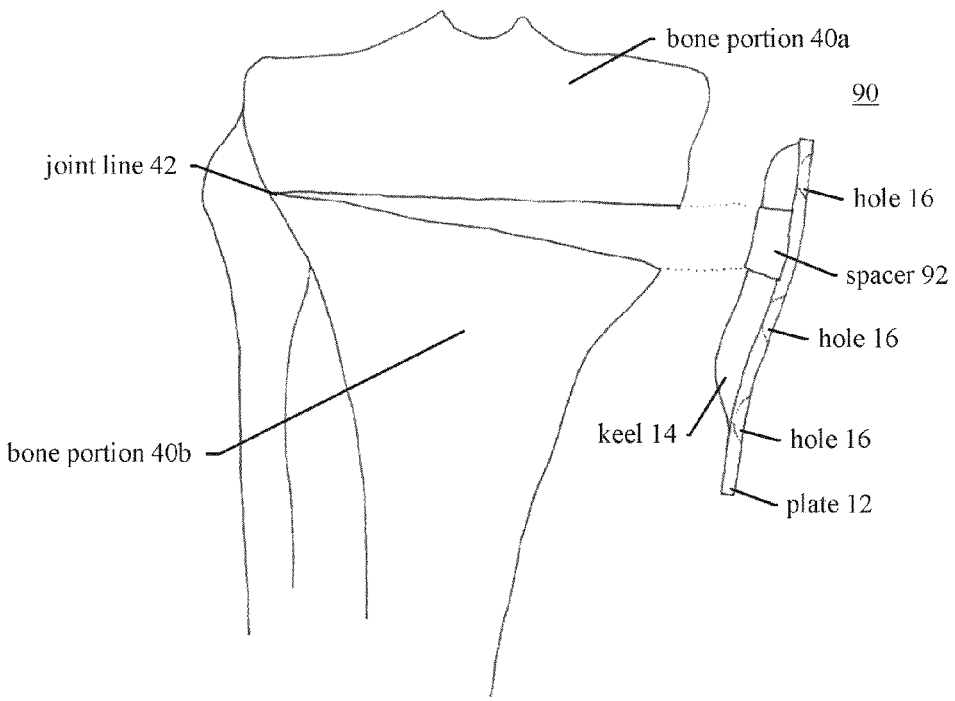
FIGS. 15A and 15B illustrate an example of a bone plate system with a plate fastened to bone portions, in accordance with various aspects of the subject disclosure.
Figure 15B:
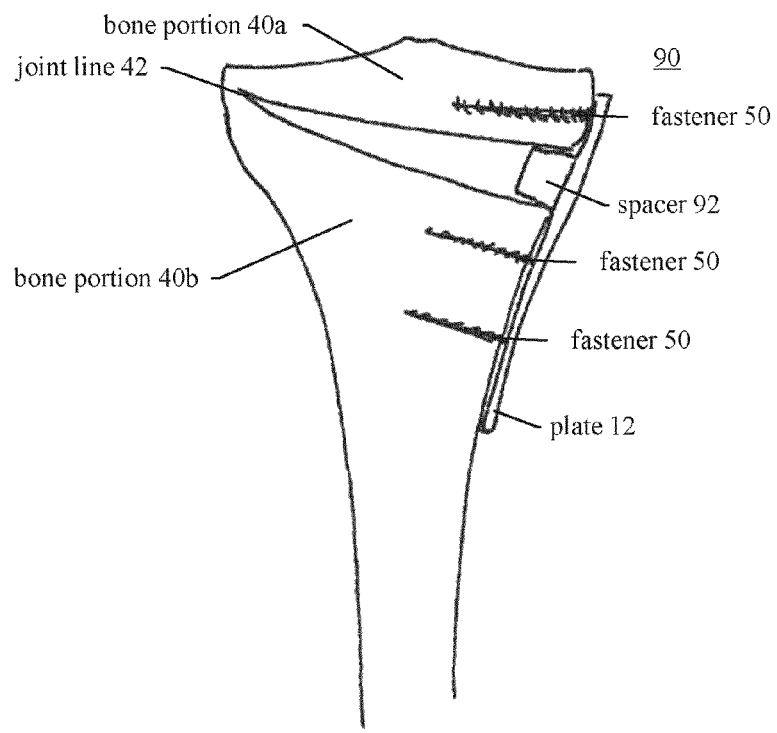

FIGS. 15A and 15B illustrate an example of bone plate system 90 with plate 12 fastened to bone portions 40, in accordance with various aspects of the subject disclosure. Bone portions 40 may be cut to form a groove in bone portions 40. Plate 12 may be fastened to bone portions 40 such that a first portion of keel 14 fits substantially within the groove of bone portion 40a, a second portion of keel 14 fits substantially within the groove of bone portion 40b, keel 14 spans joint line 42, and spacer 92 in or on at least one of plate 12 and keel 14 resides between bone portions 40.

The use of keel 14, in addition to spacer 92, while fastening plate 12 to bone portions 40 may provide the advantage of holding bone portions 40 steady relative to one another, especially when bone plate system 90 is used for osteotomies. For example, as keel 14 is positioned within the groove of bone portions 40 when plate 12 is fastened onto bone portions 40, keel 14 may reduce a horizontal movement of bone portion 40a and/or bone portion 40b with respect to each other. Thus, keel 14 may allow for a correction in placement of either bone portion 40a and/or bone portion 40b in only one plane (e.g., allows movement of bone portions 40 only along plane of keel 14) and helps reduce translational and/or rotational forces acting on bone portions 40. Spacer 92 may reduce a vertical movement of bone portion 40a and/or bone portion 40b with respect to each other.

Figure 16:
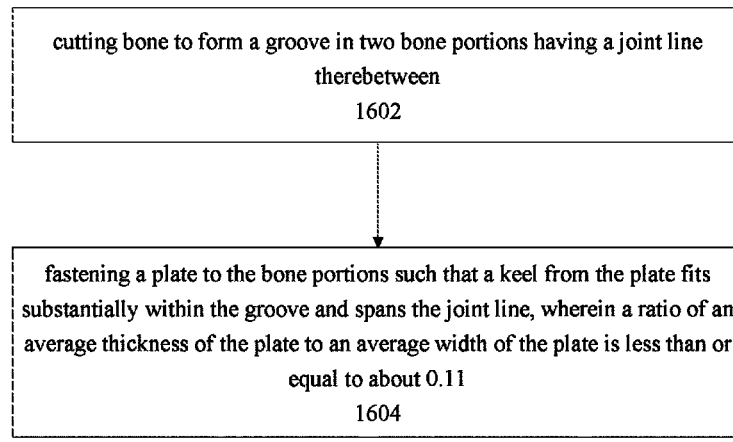
FIG. 16 illustrates an example of a method for stabilizing portions of bone, in accordance with various aspects of the subject disclosure.

FIG. 16 illustrates an example of a method 1600 for stabilizing portions of bone, in accordance with various aspects of the subject disclosure. Method 1600 comprises cutting bone to form a groove in two bone portions having a joint line therebetween (1602). Method 1600 also comprises fastening a plate to the bone portions such that a keel from the plate fits substantially within the groove and spans the joint line, wherein a ratio of an average thickness of the plate to an average width of the plate is less than or equal to about 0.11 (1604).

Figure 17:
FIG. 17 illustrates an example of a method for stabilizing portions of bone, in accordance with various aspects of the subject disclosure.

FIG. 17 illustrates an example of a method 1700 for stabilizing portions of bone, in accordance with various aspects of the subject disclosure. Method 1700 comprises contacting two bone portions with a plate (1702). The bone portions have a joint line therebetween and the plate comprises a first hole at a first portion of the plate. Method 1700 also comprises inserting a first fastener through the first hole into the bone portions such that the first fastener spans the joint line (1704).

FIG. 18 illustrates an example of a method 1800 for stabilizing and compressing portions of bone, in accordance with various aspects of the subject disclosure. Method 1800 comprises affixing a plate to a first bone portion, the plate comprising a first hole at a first portion of the plate (1802). Method 1800 also comprises inserting a first fastener through the first hole into the first bone portion, and thereafter through a contact surface of the first bone portion, and thereafter through a contact surface of a second bone portion and into the second bone portion, such that when the first fastener is advanced, the contact surface of the first bone portion makes contact with the contact surface of the second bone portion (1804). Method 1800 also comprises progressively advancing the first fastener such that the first and second bone portions become aligned with each other and progressively compress against each other (1804).

Figure 19:
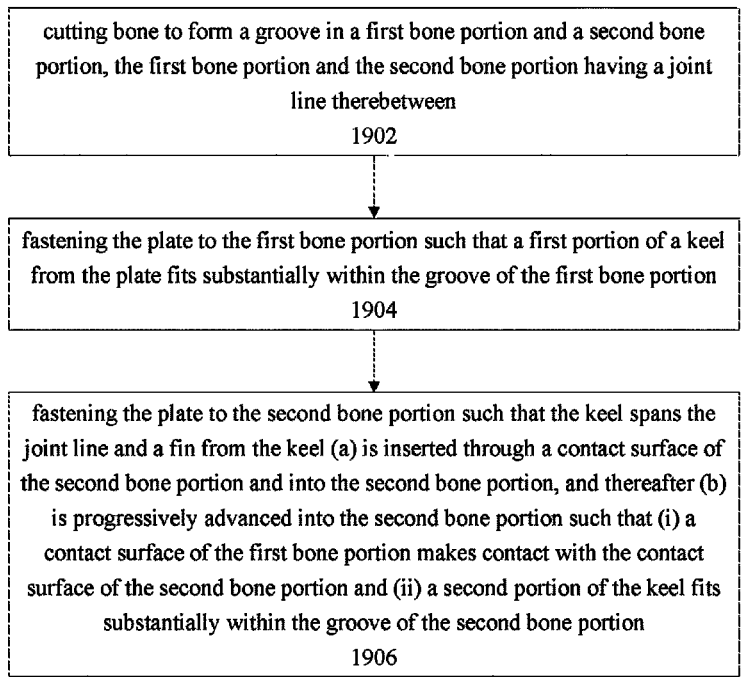
FIG. 19 illustrates an example of a method for stabilizing and compressing portions of bone, in accordance with various aspects of the subject disclosure.

FIG. 19 illustrates an example of a method 1900 for stabilizing and compressing portions of bone, in accordance with various aspects of the subject disclosure. Method 1900 comprises cutting bone to form a groove in a first bone portion and a second bone portion (1902). The first bone portion and the second bone portion have a joint line therebetween. Method 1900 also comprises fastening the plate to the first bone portion such that a first portion of a keel from the plate fits substantially within the groove of the first bone portion (1904). Method 1900 also comprises fastening the plate to the second bone portion such that the keel spans the joint line and a fin from the keel (a) is inserted through a contact surface of the second bone portion and into the second bone portion, and thereafter (b) is progressively advanced into the second bone portion such that (i) a contact surface of the first bone portion makes contact with the contact surface of the second bone portion and (ii) a second portion of the keel fits substantially within the groove of the second bone portion (1906).

FIG. 20 illustrates an example of a method 2000 for stabilizing portions of bone, in accordance with various aspects of the subject disclosure. Method 2000 comprises cutting bone to form a first groove in a first bone portion and a second bone portion having a joint line therebetween (2002). Method 2000 also comprises fastening a plate to the first and second bone portions such that a first portion of a keel from the plate fits substantially within the first groove of the first bone portion, a second portion of the keel from the plate fits substantially within the first groove of the second bone portion, the keel spans the joint line, and a spacer in or on at least one of the plate and the keel resides between the first and second bone portions (2004).

Figure 21A:
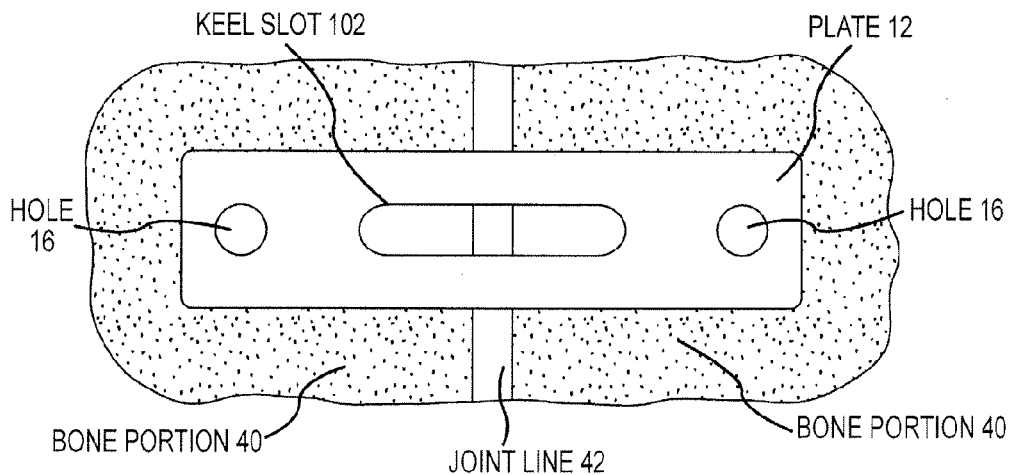
FIG. 21A illustrates a top view of an example of a bone plate system, in accordance with various aspects of the subject disclosure.

According to certain aspects of the subject disclosure, plate 12 and keel 14 may be separate from one another. Plate 12 may comprise a keel slot, and once plate 12 is fastened to bone portions, the keel slot may permit cutting of bone through the keel slot to generate a groove. Keel 14, which is separate from plate 12, may then be inserted into the groove. FIG. 21A illustrates a top view of an example of a bone plate system 100 having such a configuration, in accordance with various aspects of the subject disclosure.

Figure 21B:
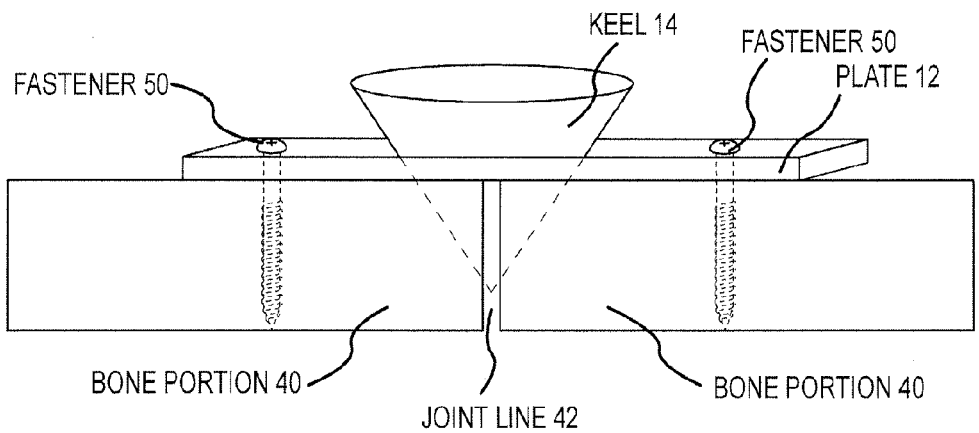
FIG. 21B illustrates a side view of a bone plate system, in accordance with various aspects of the subject disclosure.

Bone plate system 100 comprises plate 12, which is configured to be fastened to at least one bone portion (e.g., bone portions 40). Plate 12 comprises keel slot 102. FIG. 21B illustrates a side view of bone plate system 100, in accordance with various aspects of the subject disclosure. Bone plate system 100 also comprises keel 14, which is configured to extend into bone portions 40 through keel slot 102 when plate 12 is fastened to bone portions 40 (e.g., using one or more fasteners 50).

Figure 21C:
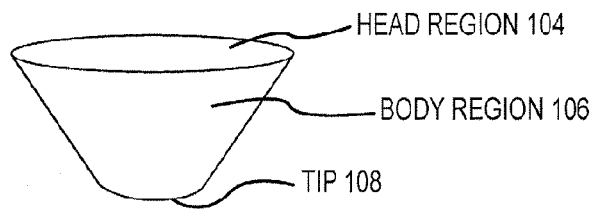
FIG. 21C illustrates an example of a keel, in accordance with various aspects of the subject disclosure.

According to certain aspects, keel slot 102 is configured to span joint line 42 when plate 12 is fastened to bone portions 40. Keel 14 is configured to span joint line 42 when keel 14 extends into bone portions 40 through keel slot 102. Keel 14 may assume a variety of shapes. FIG. 21C illustrates an example of keel 14, in accordance with various aspects of the subject disclosure. As shown in this figure, keel 14 comprises head region 104 and body region 106. Tip 108 of keel 14 may be curved. However, tip 108 may be sharp (e.g., as shown in FIG. 21B) or assume other suitable shapes.

According to various aspects of the subject disclosure, plate 12 comprises a locking assembly. In some aspects, the locking assembly is configured to substantially prevent keel 14 from dislodging from plate 12 and/or bone portions 40 when keel 14 extends into bone portions 40 through keel slot 102. In some aspects, the locking assembly is configured to substantially lock keel 14 to plate 12 when keel 14 extends into bone portions 40 through keel slot 102. In some aspects, the term "lock" may include its ordinary meaning and/or may include secure, fasten, or some other manner in which keel 14 couples to plate 12 without the use of a key or a code.

Figure 22A:
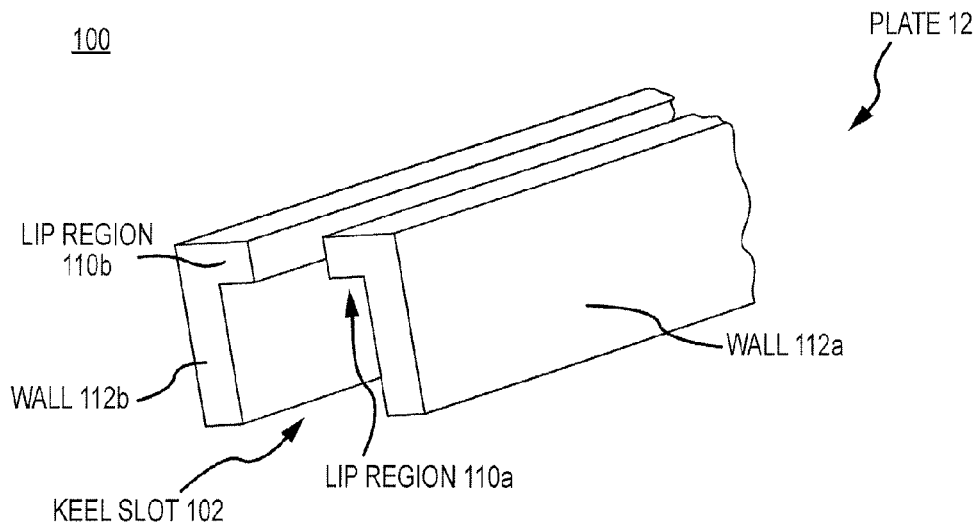
FIG. 22A illustrates an example of a locking assembly, in accordance with various aspects of the subject disclosure.

FIG. 22A illustrates an example of the locking assembly, in accordance with various aspects of the subject disclosure. The locking assembly comprises lip regions (e.g., 110a and 110b) extending along respective walls (e.g., 112a and 112b) of keel slot 102. In some aspects, wall 112a is opposite wall 112b. In some aspects, the locking assembly is configured to flex between a first state and a second state. Lip regions 110a and 110b are farther apart from one another in the first state than when lip regions 110a and 110b are in the second state. Thus, lip regions 110a and 110b may be flexed apart from one another to allow keel 14 to be inserted into keel slot 102. Although only one lip region is shown per wall of keel slot 102, the locking assembly may have any suitable number of lip regions extending along a wall of keel slot 102.

According to certain aspects, lip regions 110a and 110b may be angled from respective walls 112a and 112b at various suitable angles. For example, lip regions 110a and 110b may be angled toward bone portions 40 at less than or equal to 90 degrees from respective walls 112a and 112b when plate 12 is fastened to bone portions 40. Such a configuration may facilitate one-way insertion of keel 14 into keel slot 102, lock keel 14 to plate 12 when keel 14 extends into bone portions 40 through keel slot 102, and/or prevent keel 14 from dislodging from plate 12 and/or bone portions 40 when keel 14 extends into bone portions 40 through keel slot 102.

Figure 22B:
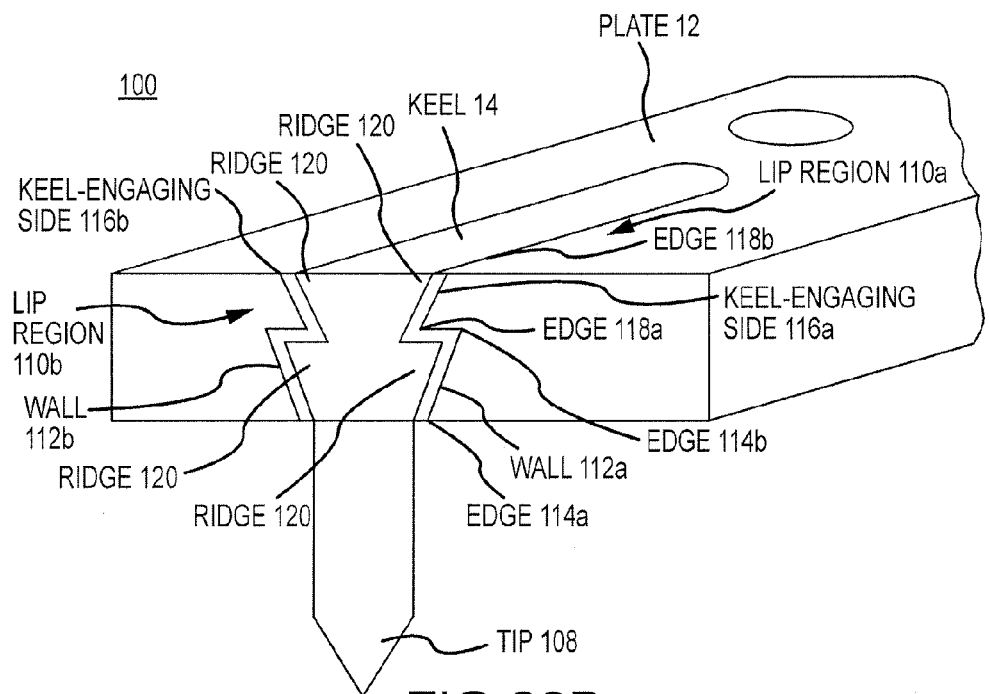
FIG. 22B illustrates an example of a locking assembly, in accordance with various aspects of the subject disclosure.

FIG. 22B illustrates another example of the locking assembly, in accordance with various aspects of the subject disclosure. Wall 112a may be slanted such that keel slot 102 is narrower at edge 114a than at edge 114b, wherein edge 114a is closer to bone portions 40 than edge 114b when plate 12 is fastened to bone portions 40. In some aspects, keel-engaging side 116a of lip region 110a is slanted such that keel slot 102 is narrower at edge 118a than at edge 118b, wherein edge 118a is closer to bone portions 40 than edge 118b when plate 12 is fastened to bone portions 40. In some aspects, wall 112a and keel-engaging side 116a are slanted at substantially the same angle. In some aspects, keel 14 comprises one or more ridges 120 extending along a first side of keel 14. The one or more ridges 120 may be sized to fit against wall 112a and lip region 110a. Such a configuration may facilitate one-way insertion of keel 14 into keel slot 102, lock keel 14 to plate 12 when keel 14 extends into bone portions 40 through keel slot 102, and/or prevent keel 14 from dislodging from plate 12 and/or bone portions 40 when keel 14 extends into bone portions 40 through keel slot 102. A similar configuration may be implemented on wall 112b, lip region 110b, keel-engaging side 116b, and/or a second side of keel 14 opposite the first side of keel 14.

Figure 23:
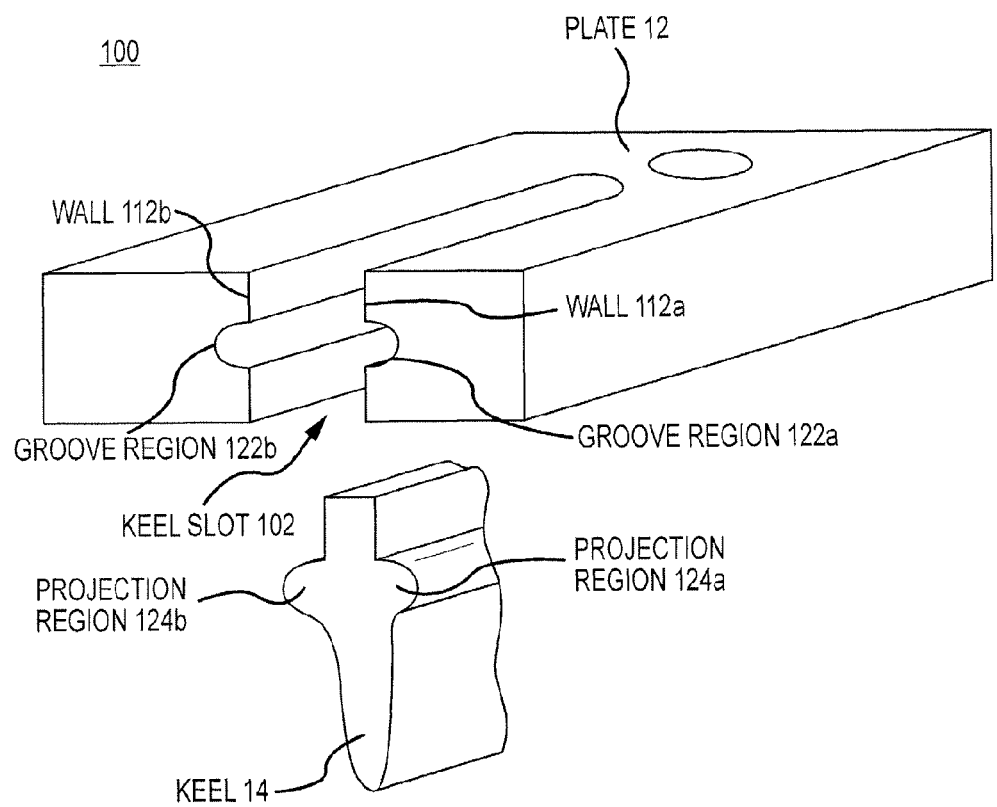
FIG. 23 illustrates an example of a locking assembly, in accordance with various aspects of the subject disclosure.

FIG. 23 illustrates another example of the locking assembly, in accordance with various aspects of the subject disclosure. The locking assembly comprises groove regions 122a and 122b extending along respective walls 112a and 112b of keel slot 102. In some aspects, keel 14 comprises projection regions 124a and 124b. Projection region 124a extends along a first side of the keel, and projection region 124b extends along a second side of the keel that is opposite the first side. Projection regions 124a and 124b are sized to fit within respective groove regions 122a and 122b when keel 114 extends into bone portions 40. In some aspects, walls 112a and 112b may be flexed apart from one another to allow keel 114 to be inserted into keel slot 102 such that projection regions 124a and 124b fit within respective groove regions 122a and 122b. Such a configuration may lock keel 14 to plate 12 when keel 14 extends into bone portions 40 through keel slot 102 and/or prevent keel 14 from dislodging from plate 12 and/or bone portions 40 when keel 14 extends into bone portions 40 through keel slot 102. Although only a single groove region is shown on a wall of keel slot 102, any suitable number of groove regions may be implemented on a wall of keel slot 102. Although only a single projection region is shown on a side of keel 14, any suitable number of projection regions may be implemented on a side of keel 14.

Figure 24A:
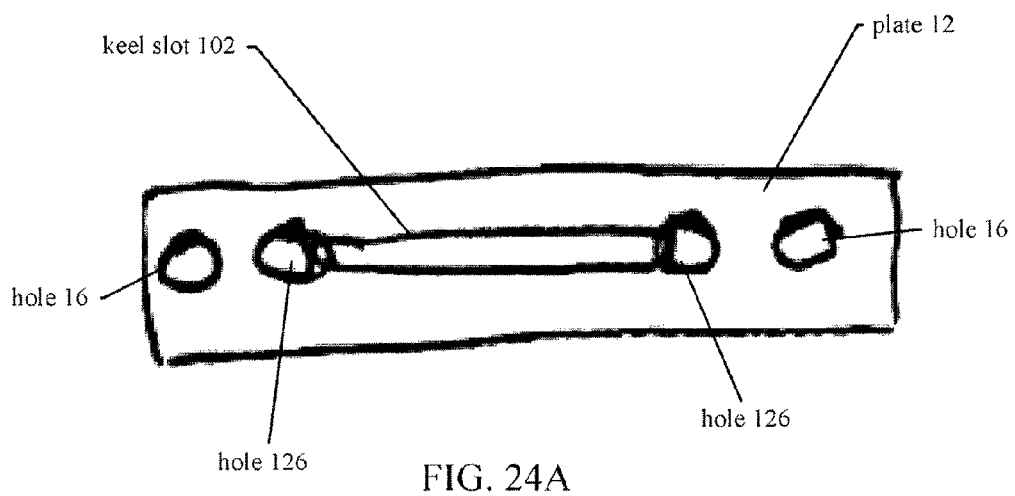
FIGS. 24A, 24B, and 24C illustrate an example of a locking assembly, in accordance with various aspects of the subject disclosure.
Figure 24B:
Figure 24C:
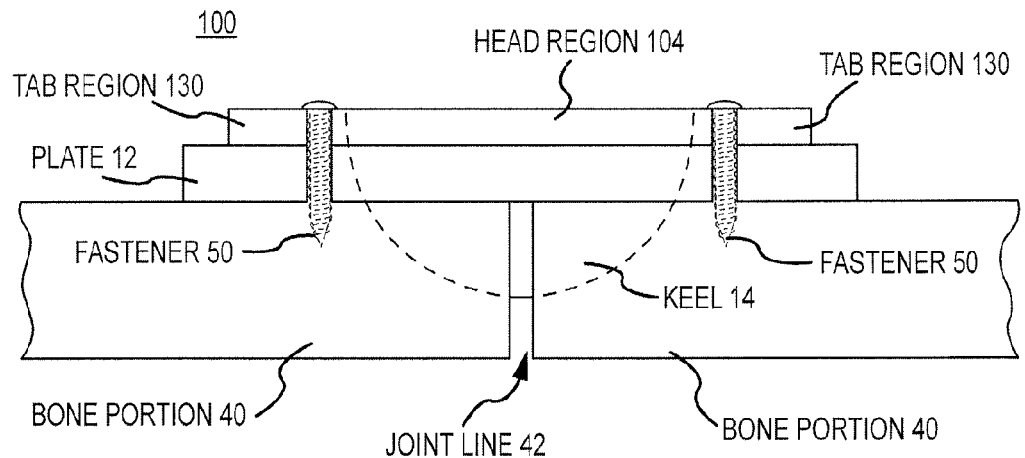

FIGS. 24A, 24B, and 24C illustrate another example of the locking assembly, in accordance with various aspects of the subject disclosure. In a top view of plate 12, as shown in FIG. 24A, the locking assembly comprises one or more fastener holes 126 formed on plate 12. In a top view of keel 14, as shown in FIG. 24B, keel 14 comprises one or more corresponding fastener holes 128. The one or more fastener holes 126 and 128 may each receive a fastener therethrough for fastening keel 14 to plate 12 when keel 14 extends into bone portions 40.

According to certain aspects, keel 14 comprises one or more tab regions 130. A corresponding fastener hole 128 is formed on each of the one or more tab regions 130. As shown in FIGS. 24A, 24B, and 24C, the one or more tab regions 30 extend from head region 104 and are configured to engage the one or more fastener holes 126 of plate 12 when keel 14 extends into bone portions 40. For example, the one or more tab regions 30 may be positioned such that the fastener holes 126 of plate 12 are aligned with the one or more corresponding fastener holes 128 of keel 14. In this way, one or more fasteners 50 may be inserted through the one or more fastener holes 126 and the one or more corresponding fastener holes 128 to lock keel 14 to plate 12 and/or fasten plate 12 to bone portions 40. In some aspects, other fasteners may be used to fasten plate 12 to bone portions 40 (e.g., using holes 16 on plate 12). Any of the fasteners used to fasten plate 12 to bone portions 40 may or may not span joint line 42 when the fasteners are used to fasten plate 12 to bone portions 40.

Figure 25:
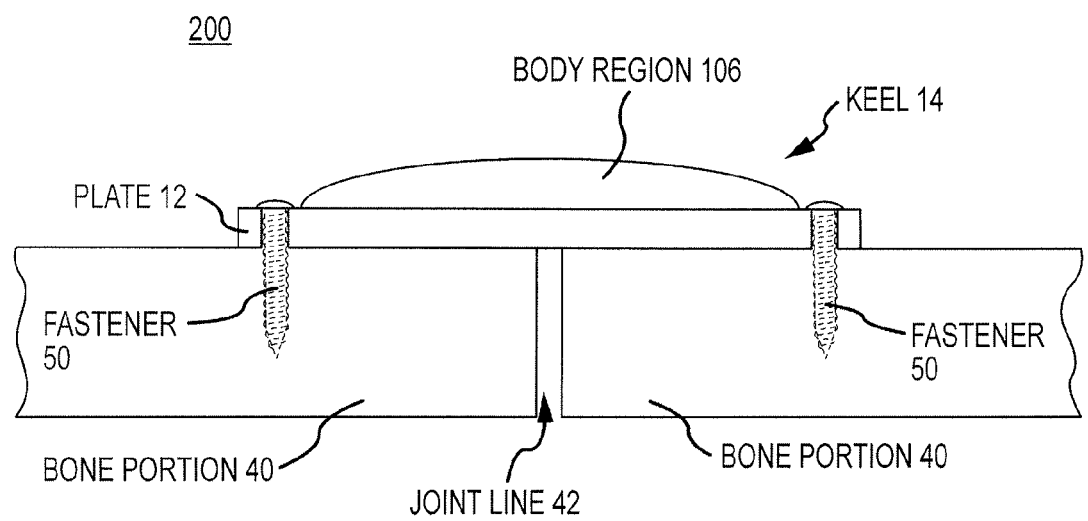
FIG. 25 illustrates a side view of a bone plate system, in accordance with various aspects of the subject disclosure.

According to various aspects of the subject disclosure, keel 14 may also project from other surfaces of plate 12. FIG. 25 illustrates a side view of bone plate system 200, in accordance with various aspects of the subject disclosure. Bone plate system 200 may be used for stabilizing bone portions 40, and comprises plate 12 and keel 14. Plate 12 is configured to be fastened to bone portions 40. Keel 14 extends from plate 12 in a direction away from bone portions 40 when plate 12 is fastened to bone portions 40. For example, plate 12 comprises a first surface and a second surface, wherein the first surface is a bone engaging surface while the second surface is opposite the first surface. Keel 14 may project from the second surface in the direction away from bone portions 40. Keel 14, in this configuration, may provide structural support to prevent and/or reduce bending and/or twisting motion of plate 12. Such a configuration may be particularly useful when a relatively thin plate 12 is used and translational and/or torsional stability for bone portions 40 is not needed.

In some aspects, keel 14 may provide additional stability by contacting perimuscular fascia or other soft tissue when plate 12 is fastened to bone portions 40. In some aspects, body region 106 of keel 14 is shaped appropriately such that keel 14 does not penetrate or damage the perimuscular fascia or other soft tissue. For example, body region 106 may taper away from the plate. In some aspects, body region 106 (e.g., including its tip) is curved and/or rounded off.

According to certain aspects, keel 14 is configured to span joint line 42 when plate 12 is fastened to bone portions 40. One or more fasteners 50 may be used to fasten plate 12 to bone portions 40. In some aspects, any of the fasteners (e.g., fasteners 50) used to fasten plate 12 to bone portions 40 may or may not span joint line 42 when the fasteners are used to fasten plate 12 to bone portions 40.

According to certain aspects, keel 14 is integral with plate 12. However, keel 14 may be separate from plate 12 in certain situations, such as when plate 12 is already fastened to bone portions 40, and keel 14 is added to plate 12 to provide additional stability. In these situations, the locking assembly as described previously (e.g., with respect to FIGS. 21A, 21B, 21C, 22A, 22B, 23, 24A, 24B, and 24C) may be used in a similar manner to lock keel 14 to plate 12.

The structures described in this application (e.g., plates, keels, locking assemblies, jigs, fins, spacers, fasteners, etc.) may be made of any suitable material, such as stainless steel and/or titanium. According to certain aspects, a liner may be used between the structures to substantially prevent contact from one another (e.g., metal-to-metal contact). In some aspects, the liner may be an intervening polymer portion. In some aspects, the liner may be made of a biocompatible, deformable, and/or fatigue resistant polymer that increases the contact area between the structures (e.g., between keel 14 and plate 12). For example, the intervening polymer portion may comprise polyether ether ketone (PEEK) or other suitable materials. The shape of the liner may conform to any of the areas of contact between the structures. In some aspects, the liner may comprise a removal member that is configured to facilitate its removal from the areas of contact. For example, the liner may comprise a tooth, a divot, a lip, or some other suitable mechanical member to facilitate removal.

Figure 26A:
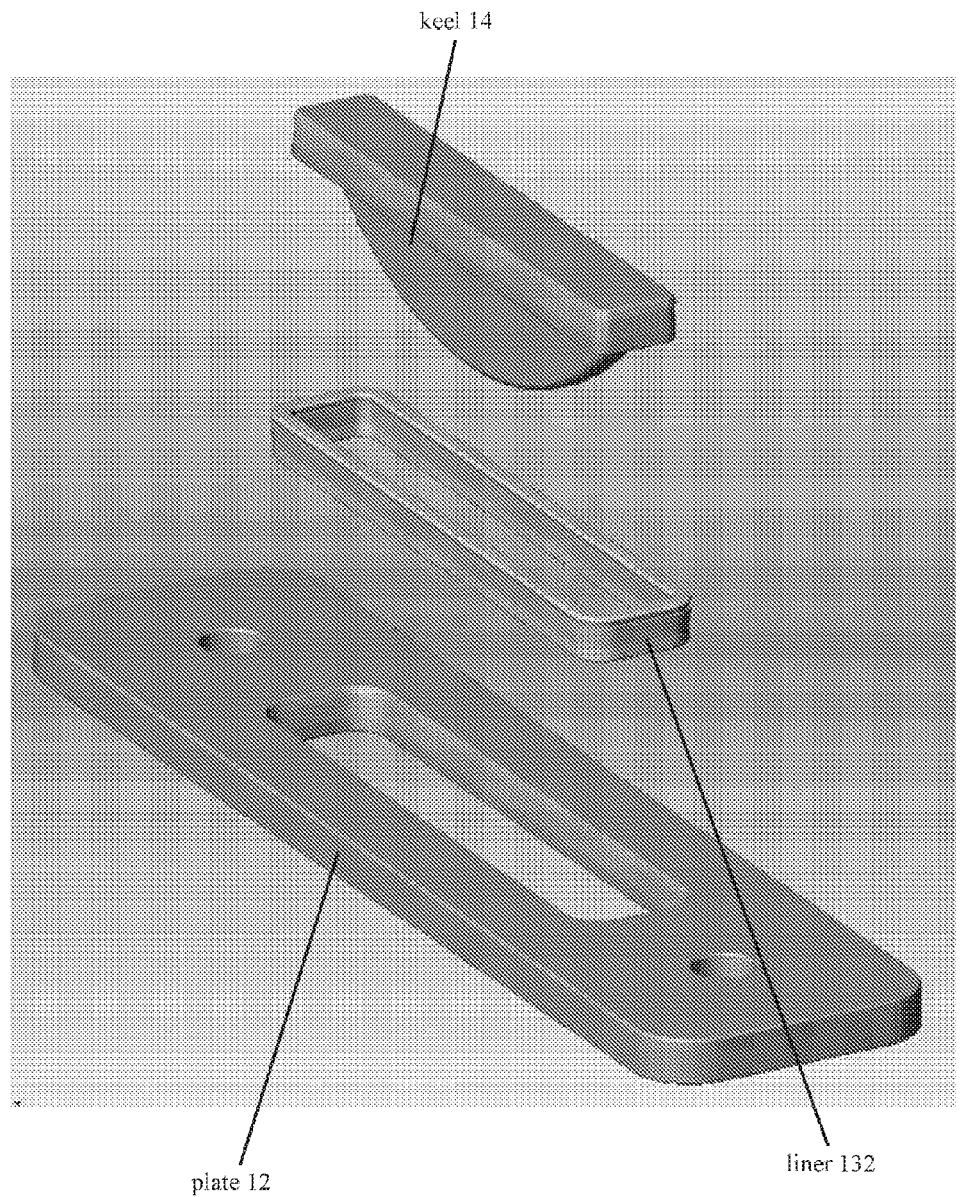
FIGS. 26A, 26B, 26C, 26D, and 26E illustrate various views of a liner being used to prevent contact between a keel and a plate, in accordance with various aspects of the subject disclosure.
Figure 26B:
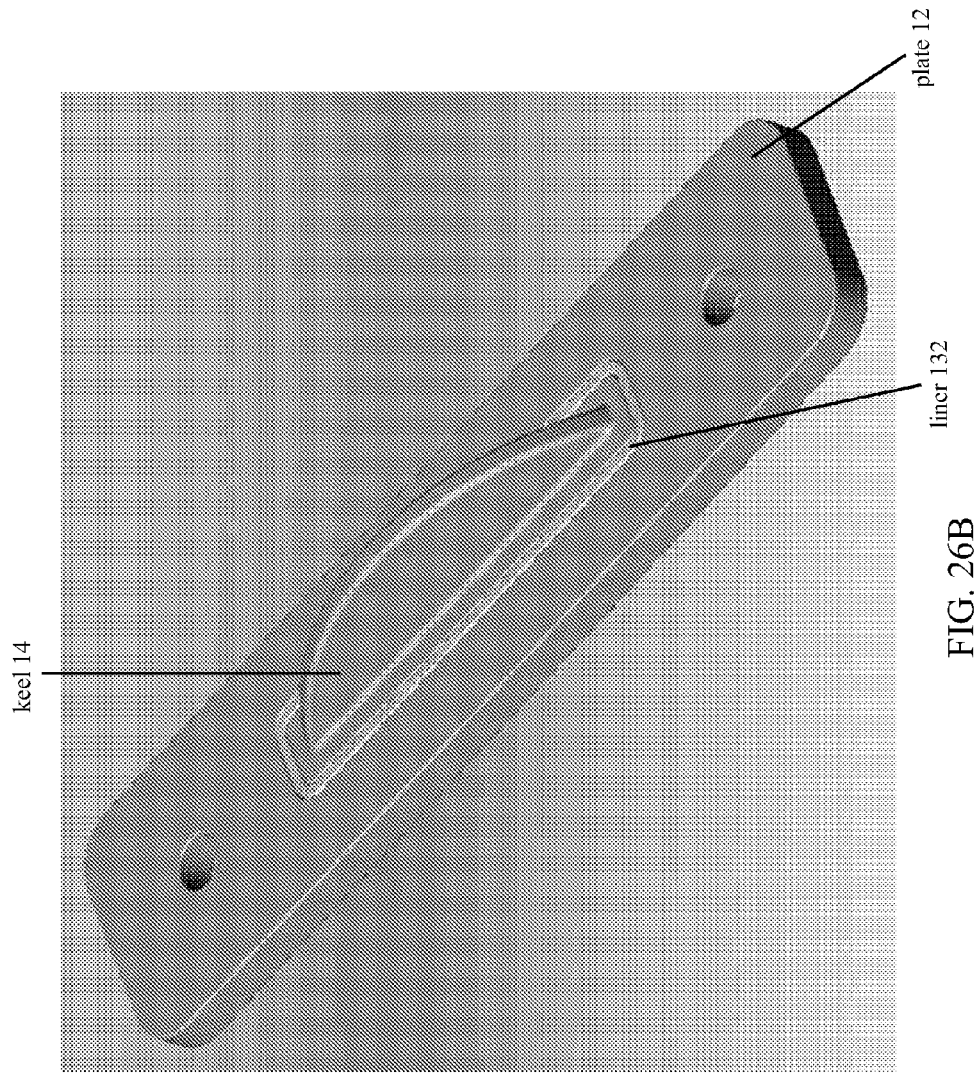
Figure 26C:
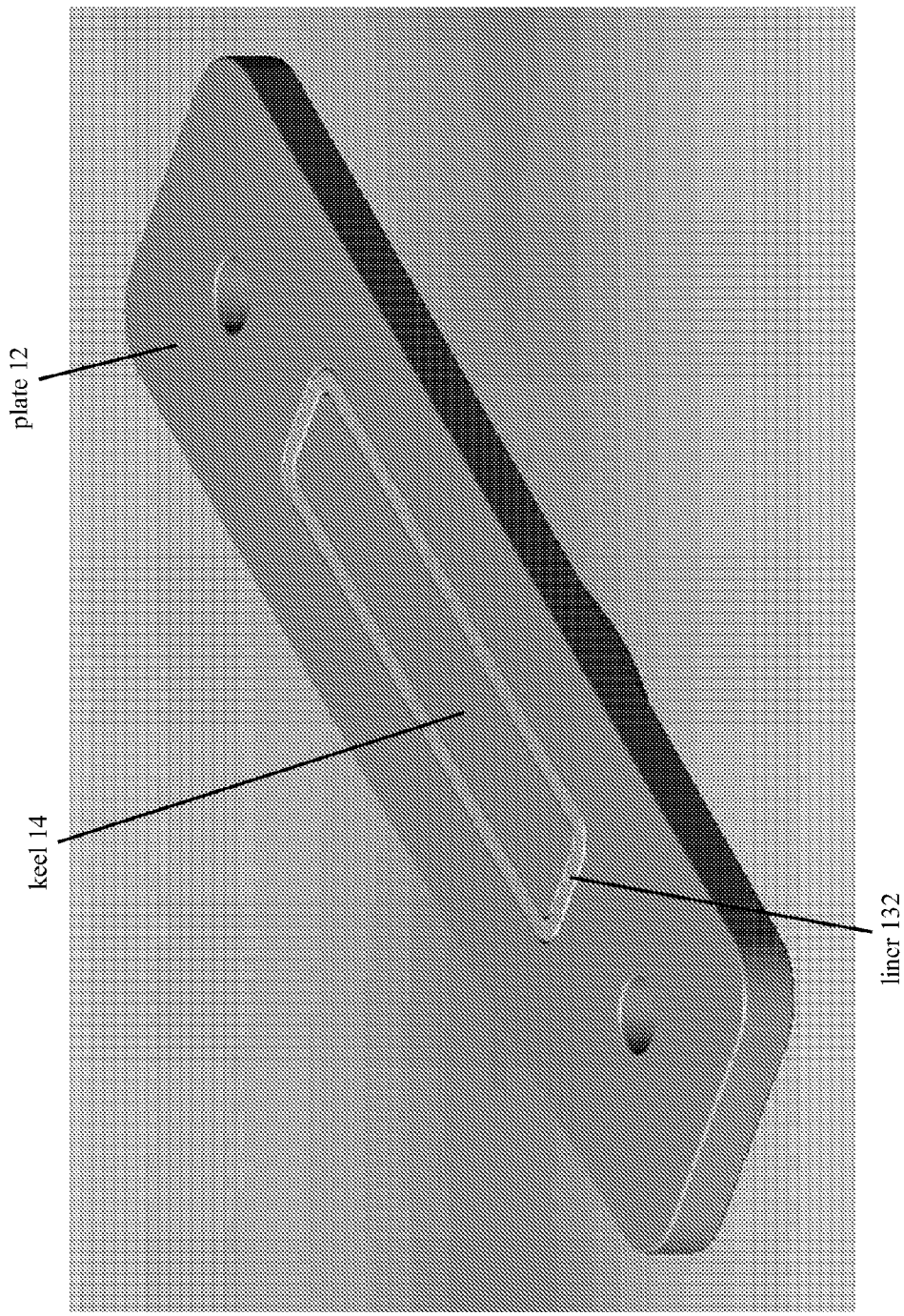
Figure 26D:
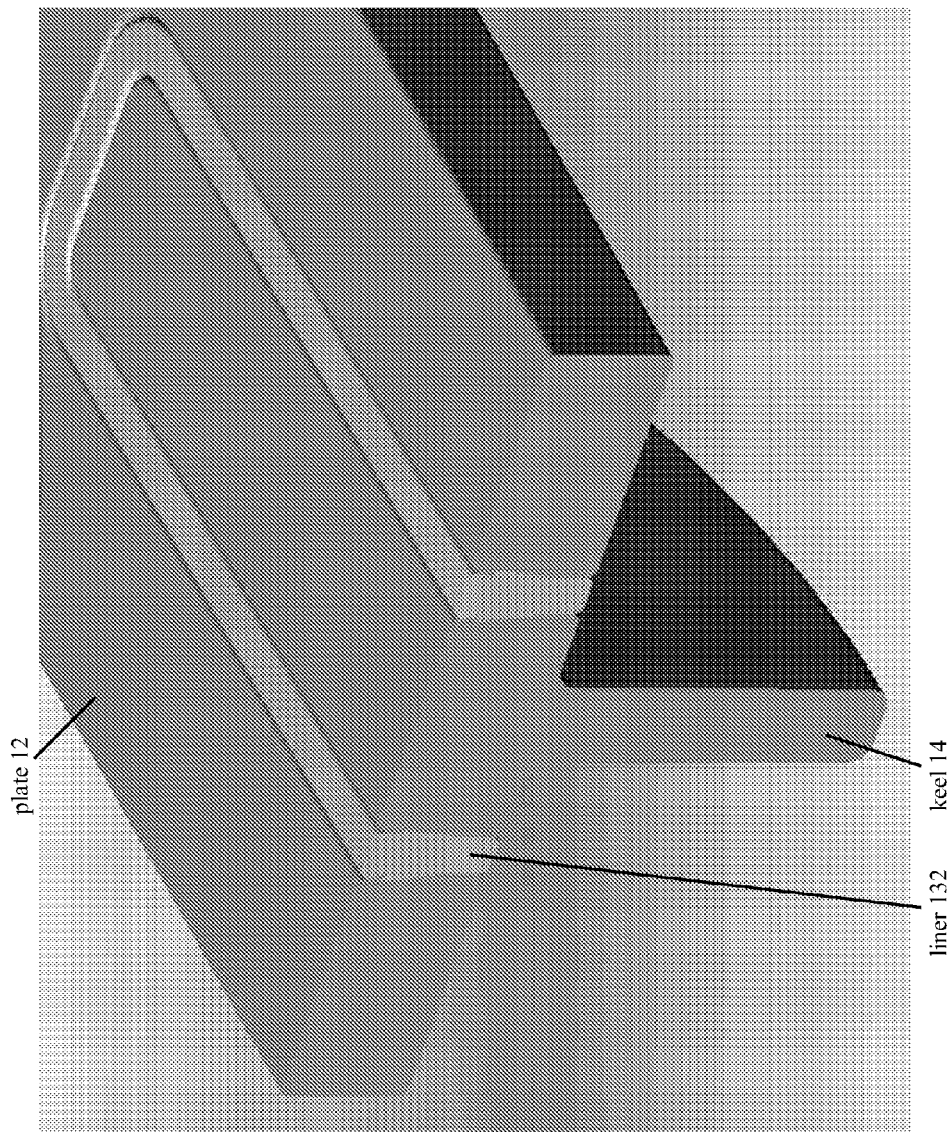
Figure 26E:
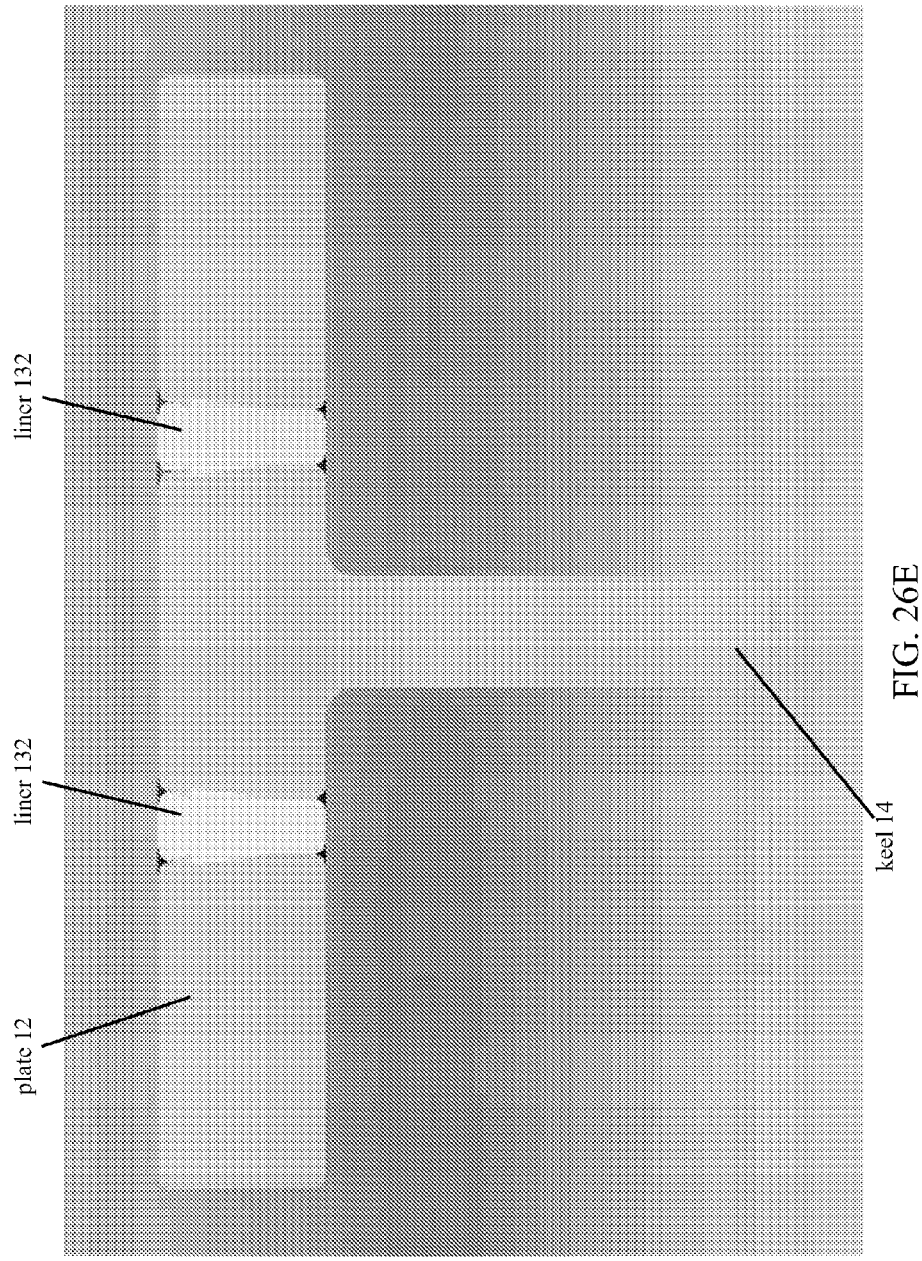

According to certain aspects, the liner may increase the contact area between keel 14 and plate 12. For example, the liner may be placed in keel slot 102 between keel 14 and plate 12 to reduce mechanical micro-motion and improve fatigue resistance. FIGS. 26A, 26B, 26C, 26D, and 26E illustrate various views of liner 132 being used to prevent contact between keel 14 and plate 12, in accordance with various aspects of the subject disclosure. FIG. 26A is an exploded view of plate 12, liner 132, and keel 14. FIG. 26B is a bottom perspective view of plate 12, liner 132, and keel 14. FIG. 26C is a top perspective view of plate 12, liner 132, and keel 14. FIGS. 26D and 26E are cross-sectional views of plate 12, liner 132, and keel 14. As shown in these figures, liner 132 may conform to the surfaces of keel 14 and plate 12, even if plate 12 comprises various lip regions and keel 14 comprises various ridges (e.g., as described with respect to FIGS. 22A and 22B).

Figure 27A:
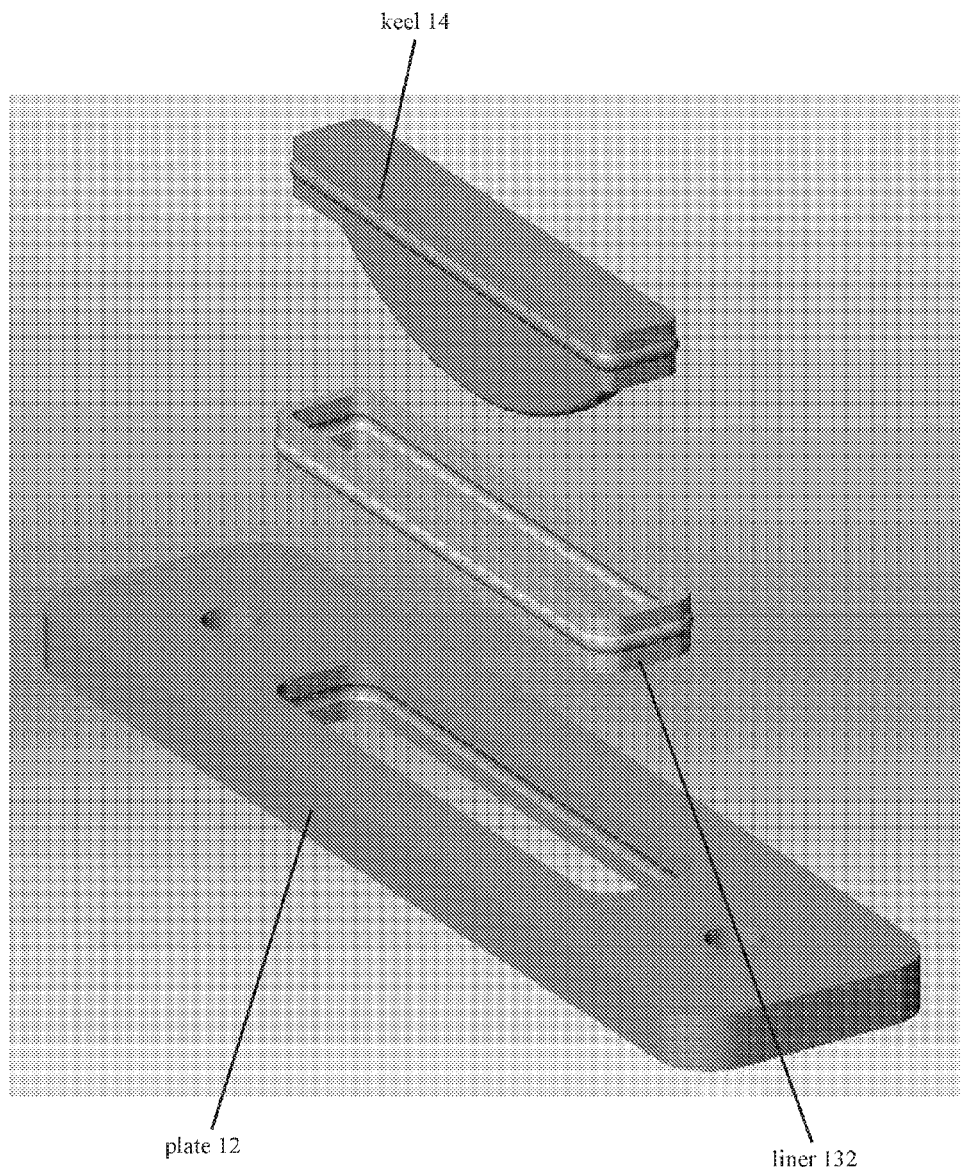
Figure 27B:
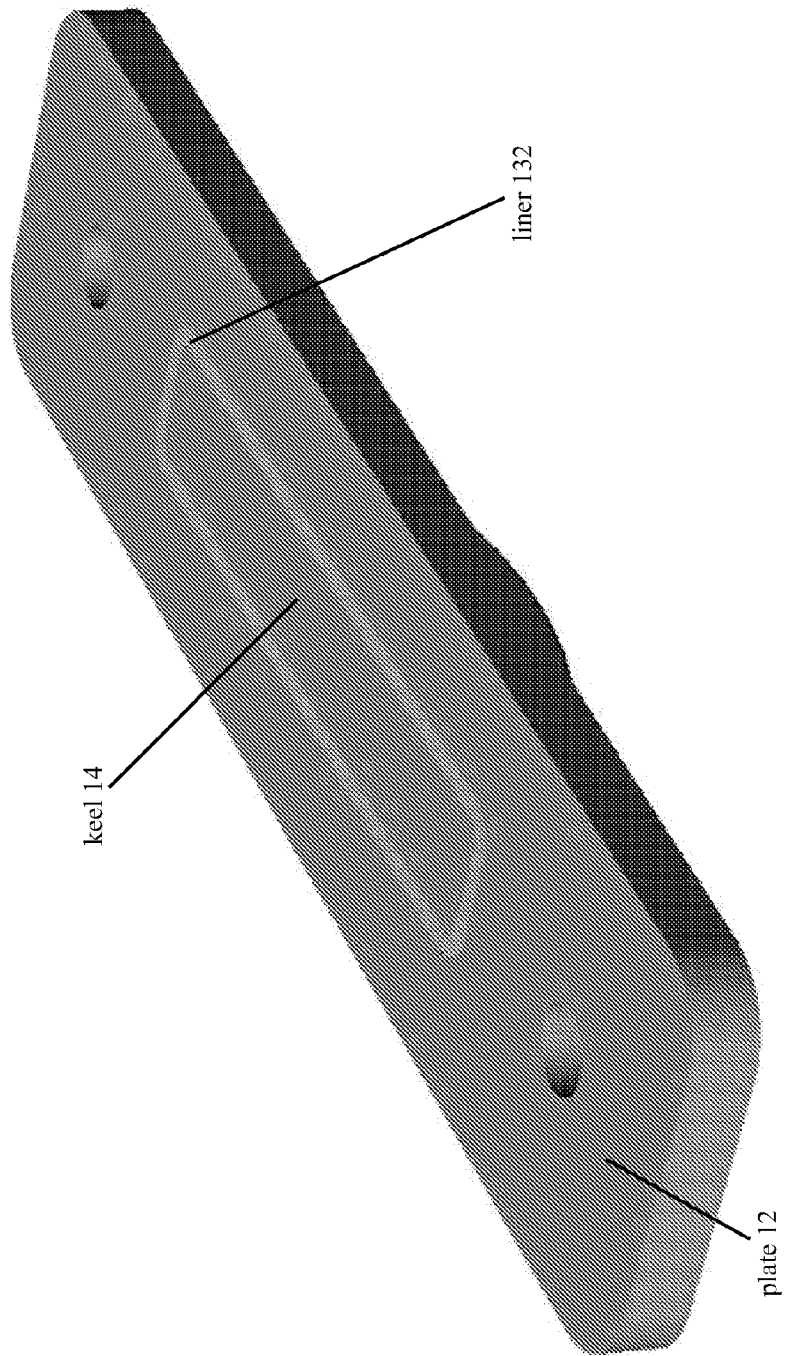
Figure 27D:
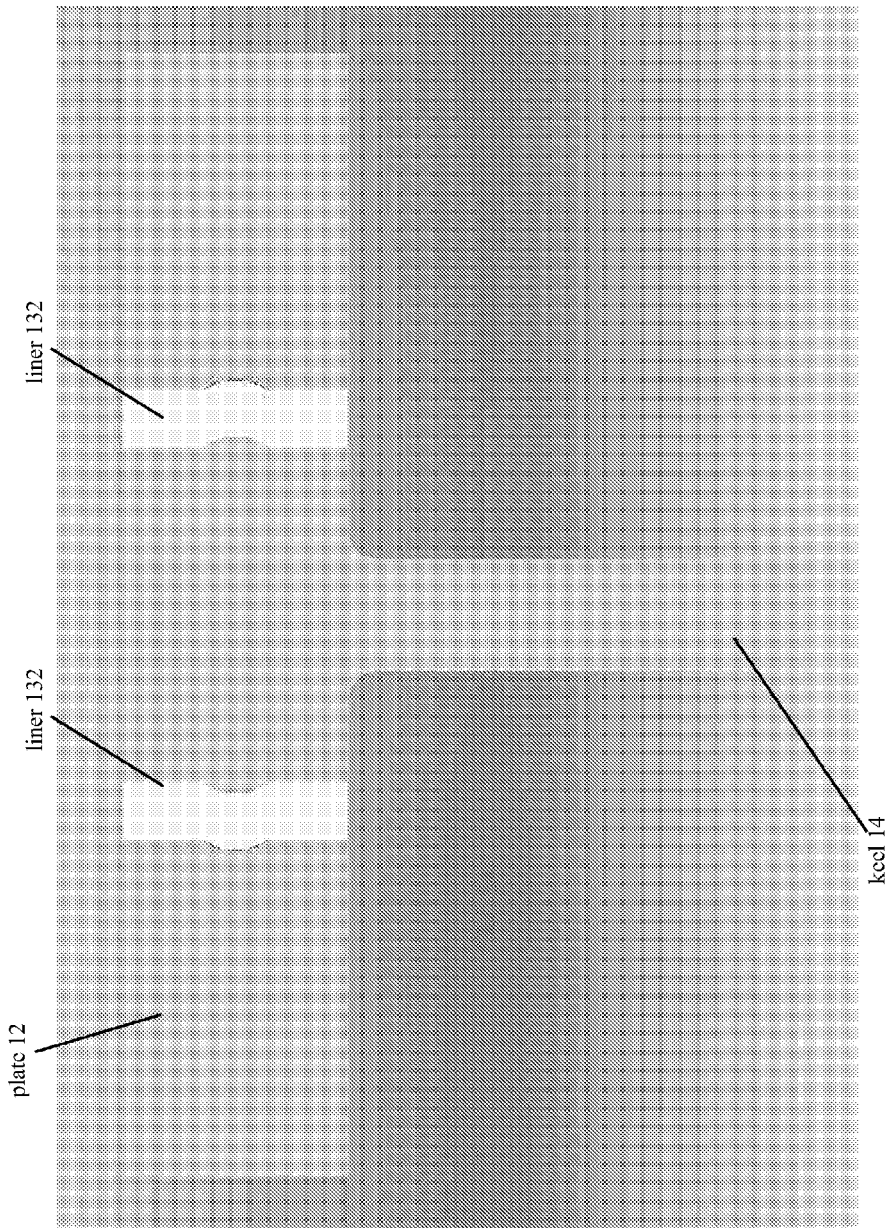

FIGS. 27A, 27B, 27C, and 27D illustrate various views of liner 132 being used to prevent contact between keel 14 and plate 12, in accordance with various aspects of the subject disclosure. FIG. 27A is an exploded view of plate 12, liner 132, and keel 14. FIG. 27B is a top perspective view of plate 12, liner 132, and keel 14. FIGS. 27C and 27D are cross-sectional views of plate 12, liner 132, and keel 14. As shown in these figures, liner 132 may conform to the surfaces of keel 14 and plate 12, even if plate 12 comprises various groove regions and keel 14 comprises projection regions (e.g., as described with respect to FIG. 23).

FIG. 28 illustrates an example of a method 2800 for stabilizing portions of bone, in accordance with various aspects of the subject disclosure. Method 2800 comprises fastening a plate to at least one bone portion, the plate having a keel slot and a locking assembly (2802). Method 2800 also comprises extending a keel into the at least one bone portion through the keel slot (2804). Method 2800 also comprises substantially preventing, with the locking assembly, the keel from dislodging from the plate when the keel extends into the at least one bone portion through the keel slot (2806).

FIG. 29 illustrates an example of a method 2900 for stabilizing portions of bone, in accordance with various aspects of the subject disclosure. Method 2900 comprises fastening a plate to at least one bone portion (2902). In some aspects, a keel extends from the plate in a direction away from the at least one bone portion when the plate is fastened to the at least one bone portion.

The methods and systems described herein may be applied anywhere in a skeleton. For example, the methods and systems described herein may be applied to bones of the axial spine and/or the appendicular skeleton. In another example, the plate systems as described herein may be used as a wrist fusion plate system, an ankle fusion plate system, and/or a metatarsal fusion plate system. The methods and systems described herein are not limited to human skeletons but may also be applied to animal skeletons as well.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

In some aspects, the phrase "substantially" as used herein refers to being within at least 99%. For example, when a keel of a plate fits substantially within a groove, the keel may fit within at least 99% of the groove. In some aspects, the phrase "substantially" as used herein refers to being within at least 95%. In some aspects, the phrase "substantially" as used herein refers to being within at least 90%. In some aspects, the phrase "substantially" as used herein refers to being within at least 80%. In some aspects, the phrase "substantially" as used herein refers to being within at least 70%. In some aspects, the phrase "substantially" as used herein refers to being within at least 60%. In some aspects, the phrase "substantially" as used herein refers to being within at least 50%. In some aspects, the phrase "substantially" as used herein is given its ordinary meaning.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A bone plate system, for stabilizing portions of bone, comprising:
    a plate configured to be fastened to at least one bone portion and having a top side which faces away from the bone portion in use and a bottom side which faces toward the bone portion in use, the plate having a keel slot having a first wall and a locking assembly; and
    a keel configured to extend into the at least one bone portion through the keel slot,
    wherein the locking assembly comprises a first lip region having a lip region first edge and a lip region second edge and extending along a first wall of the keel slot, the first wall having a first wall first edge and a first wall second edge and a keel-engaging side, and wherein the first wall is slanted such that the keel slot is narrower at the first edge of the first wall than at the second edge of the first wall, the first edge of the first wall being closer to the bottom side than the second edge of the first wall and a keel-engaging side of the first lip region is slanted such that the keel slot is narrower at a first edge of the first lip region than at a second edge of the first lip region, the first edge of the first lip region being closer to the bottom side than the second edge of the first lip region.

2. The system of claim 1, wherein the locking assembly comprises a second lip region extending along a second wall of the keel slot, the second wall being opposite the first wall.

3. The system of claim 2, wherein the locking assembly is configured to flex between a first state and a second state, and wherein the first and second lip regions are farther apart from one another in the first state than when the first and second lip regions are in the second state.

4. The system of claim 2, wherein the second lip region is angled toward the bottom side at less than or equal to 90 degrees from the second wall.

5. The system of claim 1, wherein the first lip region is angled toward the bottom side at less than or equal to 90 degrees from the first wall.

6. The system of claim 1, wherein the first wall and the keel-engaging side of the first lip region are slanted at substantially the same angle.

7. The system of claim 1, wherein the keel comprises one or more ridges extending along a first side of the keel, the one or more ridges sized to fit against the first wall and the first lip region.

8. A bone plate system, for stabilizing portions of bone, comprising:
    a plate configured to be fastened to at least one bone portion and having a top side which faces away from the bone portion in use and a bottom side which faces toward the bone portion in use, the plate having a keel slot having a first wall which includes a component extending in the direction between the top side and the bottom side and an up-ward facing component extending in a direction perpendicular to the direction between the top side and the bottom side and the plate including a locking assembly; and
    a keel configured to extend into the at least one bone portion through the keel slot, wherein the locking assembly comprises the keel having a downward facing surface which engages the upward facing surface of the keel slot so as to lock the keel in the keel slot against a downward force.

9. A bone plate system, for stabilizing portions of bone, as set forth in claim 8 wherein the upward facing component of the keel slot is a lip edge.

10. A bone plate system, for stabilizing portions of bone, as set forth in claim 9 wherein the keel slot has a top opening and a bottom opening and the upward facing component slants from a keel slot top opening toward a keel slot bottom opening.

11. A bone plate system, for stabilizing portions of bone, as set forth in claim 8 wherein the keel slot has a first wall and an opposing second wall and both walls include an up-ward facing component and the keel has a first downward facing surface which engages the first wall and a second downward facing surface which engages the second wall.

* * * * *